United States Patent
Buechler et al.

(10) Patent No.: US 9,580,756 B2
(45) Date of Patent: Feb. 28, 2017

(54) STRATIFICATION OF LEFT-SIDE AND RIGHT-SIDE COLON CANCER

(71) Applicant: University of Notre Dame, Notre Dame, IN (US)

(72) Inventors: Steven Buechler, Granger, IN (US); Amanda B. Hummon, Granger, IN (US)

(73) Assignee: UNIVERSITY OF NOTRE DAME DU LAC, Notre Dame, IN (US)

( * ) Notice: Subject to any disclaimer, the term of this patent is extended or adjusted under 35 U.S.C. 154(b) by 0 days.

(21) Appl. No.: 14/209,266

(22) Filed: Mar. 13, 2014

(65) Prior Publication Data

US 2015/0072878 A1  Mar. 12, 2015

Related U.S. Application Data

(60) Provisional application No. 61/852,412, filed on Mar. 15, 2013.

(51) Int. Cl.
*C12Q 1/68* (2006.01)
*G06F 19/00* (2011.01)

(52) U.S. Cl.
CPC .......... *C12Q 1/6886* (2013.01); *G06F 19/70* (2013.01); *C12Q 2600/106* (2013.01); *C12Q 2600/112* (2013.01); *C12Q 2600/158* (2013.01); *G06F 19/3431* (2013.01)

(58) Field of Classification Search
CPC .......... C12Q 1/6886; C12Q 2600/158; C12Q 2600/112
See application file for complete search history.

(56) References Cited

U.S. PATENT DOCUMENTS

2012/0172244 A1* 7/2012 Buechler et al. ................ 506/9

OTHER PUBLICATIONS

Cushman-Vokoun et al. Clinical utility of KRAS and BRAF mutations in a cohort of patients with colorectal neoplasms submitted for microsatellite instability testing. Clinical Colorectal Cancer, vol. 12, No. 3, pp. 168-178, Jun. 2013.*
Galbiati et al. A new microarray substrate for ultra-sensitive genotyping of KRAS and BRAF gene variants in colorectal cancer. PLOS ONE, vol. 8, No. 3, e59939, Mar. 2013, printed as pp. 1/12-12/12.*
POET Report: Perspectives on Emerging Technology. Prognostic Uses of MSI Testing. College of American Pathologists, Technology Assessment Committee (TAC) with input from the Council on Scientific Affairs, www.cap.org, Version No. 1, May 2011, printed as pp. 1/7-7/7.*
O'Connell et al. Relationship between tumor gene expression and recurrence in four independent studies of patients with stage II/III colon cancer treated with surgery alone or surgery plus adjuvant fluorouracil plus leucovorin. Journal of Clinical Oncology, vol. 28, No. 25, pp. 3937-3944, Sep. 1, 2010.*
Quasar Collaborative Group, et al.: Lancet 2007, 370:2020-2029.
Benson AB, et al.: J Clin Oncol 2004, 22:3408-3419.
Wang Y, et al.: J Clin Oncol 2004, 22: 1564-1571.
Jiang Y, et al.: JMD 2008, 10:346-354.
O'Connell MJ, et al.: J Clin Oncol 2010, 28:3937-3944.
Gray RG, et al.: J Clin Oncol 2011.
Bauer KM, et al.: Mol. Carcinog. 2012, 51:411-421.
Meguid RA, et al.: Ann Surg Oncol 2008, 15:2388-2394.
Buechler SA: BMC Cancer 2009, 9:243.
Jorissen RN, et al.: Clin Cancer Res 2009, 15:7642-7651.
Sorby LA, et al.: J Exp. Clin. Cancer Res. 2010, 29:144.
Chul SL, et al.: Cytotechnology 2011, 63:645-654.
Dexter DL, et al.: Am. J Med. 1981, 71 :949-956.
Eshelman JR, et al.: Oncogene 1995,10:33-37.
Bauer KM, et al.: Journal of Proteome Research, 2014, 13:4910-4918.

* cited by examiner

Primary Examiner — Jennifer Dunston
(74) Attorney, Agent, or Firm — Husch Blackwell LLP; Denise L. Mayfield

(57) ABSTRACT

Compositions/methods for employing fresh-frozen or FFPE colon cancer tissue in left side colon cancer (LCC) and right-side colon cancer (RCC) disease patients for risk of relapse assessment/stratification is provided (3 strata and a 4 strata methodology). An RCC gene panel of 4 genes (FAM69A, CDX2, FAM84A, ITGA3), and 9 genes (FAM69A, CDX2, ITGA3, FAM84A, ITPRIP, RAB3B, SMAD3, PCSK5, MMP28), is provided. An LCC gene panel of 4 genes (NOX4, WNT5A, MMP3, IBSP), and a 9 genes (MMP3, WINT5A, NOX4, IBSP, SLC16A6, CYPIBI, TFAP2C, MATN3, ANKRD6), is provided. A microchip-based clinical tool, and a kit including a microchip, is presented. The invention also describes a computer-implemented method for assessing relative risk of relapse in LCC and/or RCC disease. An individual patient scoring method that presents a continuous stratification score useful in the post-surgical colon cancer management of LCC and/or RCC patient is also presented.

7 Claims, 6 Drawing Sheets

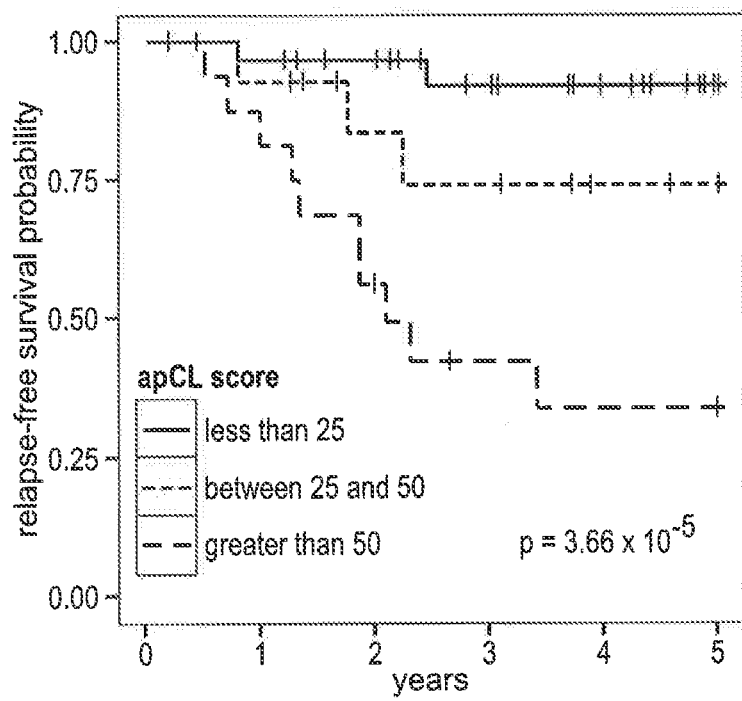
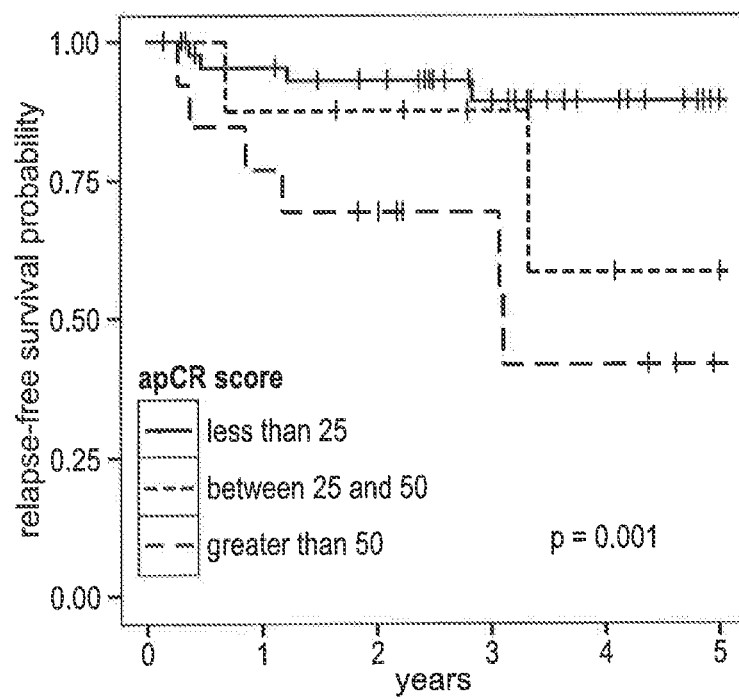

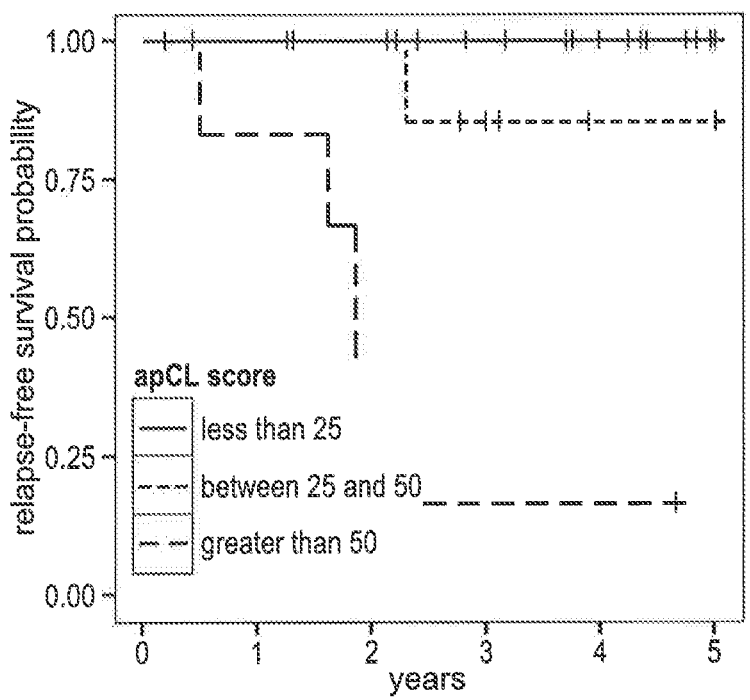
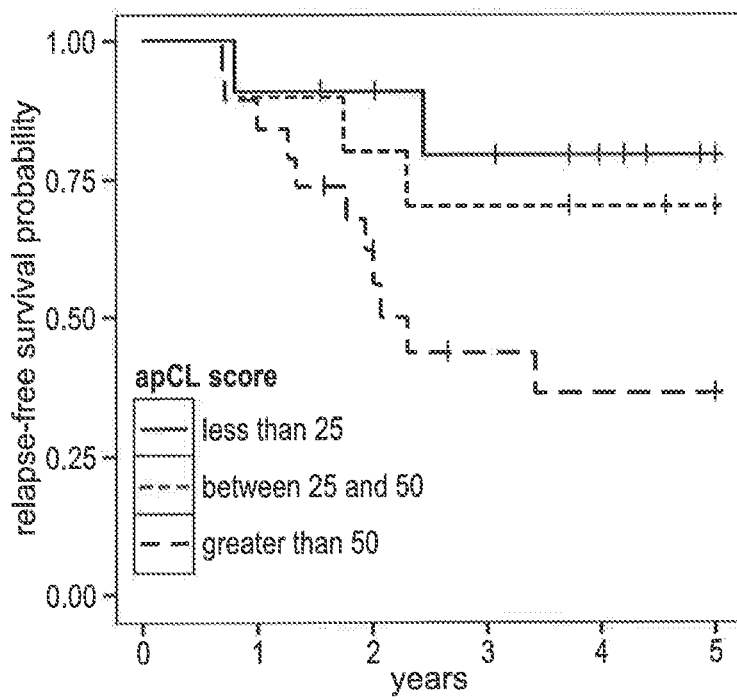

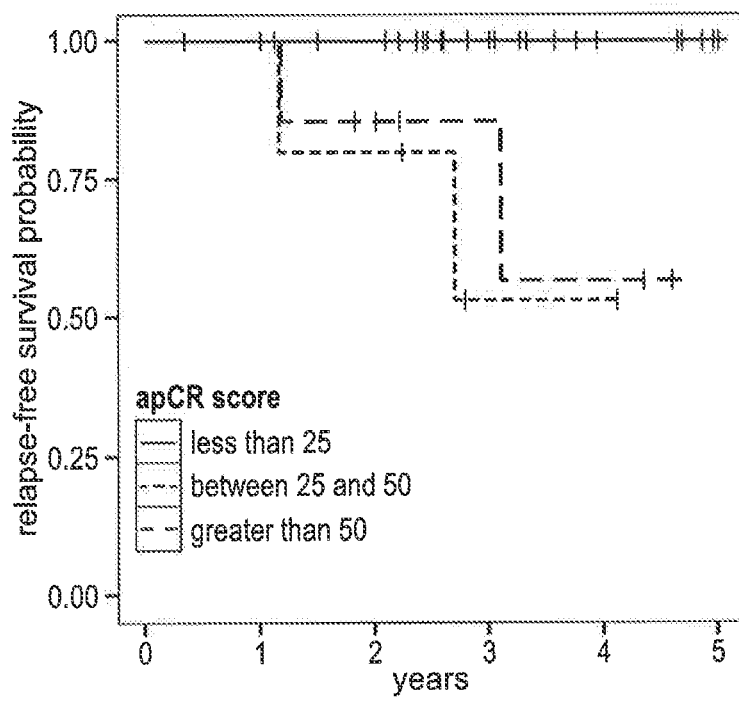
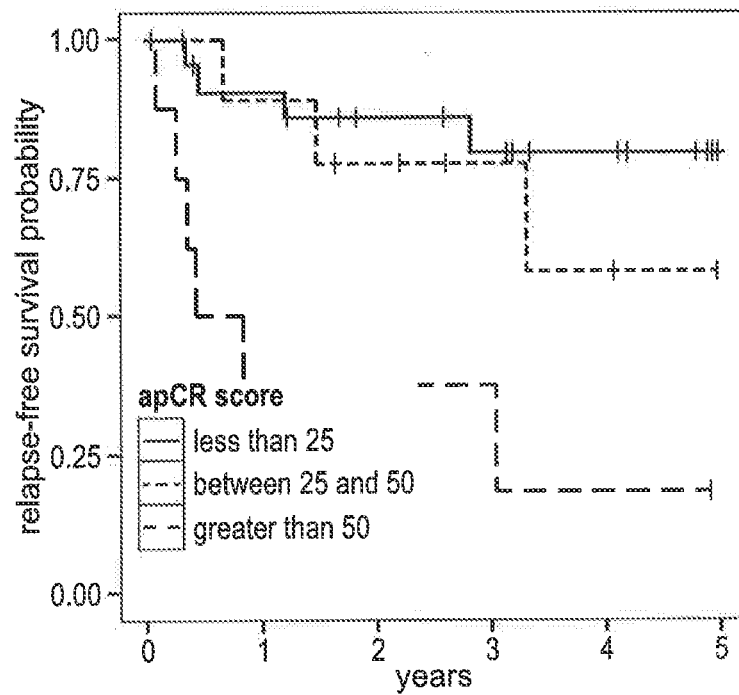

SEQUENCE LISTING

<160> NUMBER OF SEQ ID NOS: 38

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic primer -continued

<400> SEQUENCE: 1
actgctttct gttctgtcca                                           20

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gaacctgtgc gagtggatg                                            19

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tggagtttac ctggcttatt                                           20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agactaccta ctgcgtggtg                                           20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cttcctctcc tcctgatctc                                           20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gacagttcag aagaggagga g                                         21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 7
tattgaggac atgtggcttg                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgtgagacgc atgttgaagg                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cagctcttga taggtgtgct                                              20

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccagggatta atggagatg                                               19

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcctttcaag aggtaacagc                                              20

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gccatgaagc aggactctaa aga                                          23

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 13
gacccacagt ttcatttcaa                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctgggctact cagatcaaga                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gagaatgttt cgctgtgttt                                               20

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gtcaacacca agtgcatca                                                19

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gacatgcctc accagatg                                                 18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctcgccatga agaagtcc                                                 18

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 19
acttttggta cattgtggct tcaa                                          24

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tgtgatttag ggcagcag                                                 18

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tcctccggat ggtgatgtag                                               20

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cagcctccaa attcagtta                                                19

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atttccattt gatttgctgt                                               20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
caggaagaac tgaactgtgg                                               20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 25
tctcagcctc agagtcttca                                              20

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acagcacctg ggtgtagc                                                18

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gtcaccacca ccagacacac                                              20

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cacaatgata agagccactt c                                            21

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
caatttcatg agcagcaac                                               19

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tcgaatttct ctgctgagtt                                              20

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 31
ttggcataac acagctgatt gat                                           23

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggcacgactg aagtcataat                                               20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tctcttcctc catgtcacac                                               20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aagaggaggc tgtatctcca                                               20

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cggcagtaga tgacatgag                                                19

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cgaatgactg tctgatcgtg                                               20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 37
gaacttggaa gacattgcac                                              20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ccgccaggac aaaccagtat                                              20
```

STRATIFICATION OF LEFT-SIDE AND RIGHT-SIDE COLON CANCER

STATEMENT OF GOVERNMENT SUPPORT

This invention was made with government support under Grant No. T32GM075762 awarded by the National Institutes of Health and Grant No. TL1 TR000162 awarded by the National Institutes of Health. The government has certain rights in this invention. NIH training grant T32GM075762 and by the Indiana CTSI Program and NIH grant TLI TR000162.

CROSS REFERENCE TO RELATED APPLICATIONS

This application is a utility application which claims priority to the Provisional Application USSN 61/852,412, filed Mar. 15, 2013. This provisional application is specifically incorporated herein in its entirety.

SEQUENCE LISTING

The instant application contains a Sequence Listing which is submitted herewith electronically in ASCII format, and is hereby incorporated by reference in its entirety. Said ASCII copy, created on Mar. 12, 2014, is named 55145-13001_SL.txt and is 8,929 bytes in size.

BACKGROUND

Adjuvant chemotherapy significantly reduces mortality in stage III colon cancer, however it is only marginally effective in the full population of stage II colon cancer patients [1]. While oncologists may recommend chemotherapy for some patients with additional poor prognosis factors, such as involvement of the visceral peritoneum or poorly differentiated histology, a guideline from the American Society of Clinical Oncology states that "direct evidence from randomized controlled trials does not support routine use of adjuvant chemotherapy for patients with stage II colon cancer" [2].

Although the ultimate goal is a test that predicts the level of effectiveness of chemotherapy, until that goal is reached, a test that stratifies patients by prognosis may guide the choice of treatment. A prognostic test may identify patients at a very low risk of recurrence, for whom chemotherapy is unwarranted; or it may identify other patients at such a high risk of dying from cancer that chemotherapy is prudent.

Several research groups have published prognostic tests for stage II colon cancer disease based on the expression levels of specific genes [3-6]. The most thoroughly validated test is Oncotype DX Colon™ (Genomic Health, Redwood City, Calif.). Using mRNA measurements of 7 target genes, and 5 reference genes, a recurrence score (RS) is derived that, in one study [6], partitions patients into three groups with three-year expected survival percentages of 88%, 82% and 78%, for the low risk, intermediate risk and high risk groups. In the same study, the treatment benefit score (TS), which is based on the expression levels of 6 other genes, was hypothesized to identify patients who will benefit from chemotherapy; however, TS failed to be statistically significant as a predictor of treatment benefit.

The advent of microarrays and molecular genomics has the potential for a significant impact on the diagnostic capability and prognostic classification of disease, which may aid in the prediction of the response of an individual patient to a defined therapeutic regimen. Microarrays provide for the analysis of large amounts of genetic information, thereby providing a genetic fingerprint of an individual. There is much enthusiasm that this technology will ultimately provide the necessary tools for custom-made drug treatment regimens. Currently, healthcare professionals have few mechanisms to help them identify cancer patients who will benefit from chemotherapeutic agents. Identification of the optimal first-line drug has been difficult because methods are not available for accurately predicting which drug treatment would be the most effective for a particular cancer's physiology. This deficiency results in relatively poor single agent response rates and increased cancer morbidity and death. Furthermore, patients often needlessly undergo ineffective, toxic drug therapy.

A need continues to exist in the medical arts, particularly in the area of oncology, for a tool useful in identifying and stratifying colon cancer patients into a group that would most benefit from an aggressive treatment regimen apart from the patients that would not likely benefit from an aggressive post-surgical chemotherapy treatment. Such would greatly enhance the quality of life of the colon cancer patient as well as provide a greater likelihood of patient therapeutic benefit from a selected course of treatment. In particular, methods are needed to identify those stage II colon cancer patients who are at a sufficiently high risk for relapse that they may benefit from chemotherapy. The treatment of colon cancer would be significantly advanced by a diagnostic test that identifies those stage II colon cancer patients whose risk of relapse is significantly decreased by adjuvant chemotherapy.

SUMMARY OF THE INVENTION

In a general and overall sense, the present Application provides for a 3 stratification and a 4 stratification method/test that provides for an individual LCC and/or RCC patient continuous score. This patient continuous score may then be used to characterize the patient as within a specific risk of relapse strata grouping. The score assigned to each individual colon tumor sample may range from: good, fair, poor and very poor (in the 4 stratification/method test) or from low risk of relapse, moderate risk of relapse or high risk of relapse (in the 3 stratification method/test). The five-year survival probability in the poorest prognosis groups of colon cancer patients (i.e., very poor (in the 4-stratification method) and high risk of relapse (in the 3 stratification test), particularly stage II colon cancer patients, is under 0.50 in the validation cohort. Treatment with chemotherapy may be prudent in such high-risk patients. This assessment is typically the case in RCC and LCC patients having T4 disease.

The present inventors have previously demonstrated that right side colon cancer (RCC) and left-side colon cancer (LCC) follow different pathways to relapse [7]. The right side of the colon extends from the cecum or ascending colon through the transverse colon, excluding the appendix. The left side of the colon begins left of the splenic flexure, includes the descending colon and ends with the sigmoid, but does not include the rectum [8]. The present tests/methods demonstrate that the expression levels of certain sets of different genes in LCC and RCC are significantly predictive of relapse in left-side colon tumors, but not in right-side tumors. Other sets of genes were found to be prognostic in right-side tumors but not in left-side tumors. Moreover, these side-specific prognostic genes are involved in different biological processes.

Prognostic scores are provided herein that were developed separately for right-side and left-side colon cancer. The discovery sample set for this development is a microarray dataset previously described (7, 10). The resulting prognostic score for left-side colon cancer (LLC) or right side colon cancer (RCC), referred to as the apCL score or apCR score respectively, assigns to each tumor an integer score ranging from 0 to 4 (or 0 to 100), based on the assessment of expression levels of a panel of LCC genes (4 to 9, preferably 4 genes) and/or RCC genes (4 to 10, preferably 4 genes). The probability of 5-year relapse-free survival is shown according to the present tests/methods to decrease with increasing apCL score and/or an increasing apCR score (ap abbreviates "accelerated progression", and CL is for colon-left; CR is for colon right).

A clinically useful diagnostic test that is compatible with formalin-fixed, paraffin embedded (FFPE) samples suitable for use as a clinical standard, is presented. Here, validation of apCR and apCL is validated with translation of the test from one using microarray data from frozen tissue, to one using RT-PCR to measure gene expression in FFPE tissue.

The present invention and methods demonstrate that the test/methods may be used with nucleic acid obtained from archived formalin fixed paraffin-embedded (FFPE) biopsy material, as well as fresh/frozen (FF) tissue and, therefore, that the tests/methods are compatible with the most widely available type of biopsy material, FFPE tissue. The expression level of a test sample nucleic acid may be determined using CRNA, CDNA, or other artificial oligonucleotide synthesized using information derived from total RNA of a FFPE tissue, fresh frozen tissue or fresh tissue that has been stored in solutions such as RNALATER.

The validation set used in the present work is a collection of FFPE tissue samples from patients at Elkhart General Hospital, Elkhart, Ind., with stage II colon cancer (unpublished). These tissue samples included 39 left-side samples and 44 right-side samples. With the methods disclosed herein, the translated test stratifies these patients into groups with increasingly higher risk of relapse.

The present methods/test provide a clinically viable diagnostic test that may identify risk of relapse for both left side colon cancer patients and right side colon cancer patients, and in particular, colon cancer patients having a Stage II colon cancer. This information is valuable to the clinician, as it provides a guidepost against which a decision may be made concerning the relative risk of death of the patient in view of available chemotherapy or other treatment options.

Left-Side Colon Cancer—Prognostic Gene Panels:

In some embodiments, the four genes defining the left-side prognostic score, denoted anCL, are matrix metallopeptidase 3 (stromelysin 1, progelatinase) (MMP#), wingless-type MMTV integration site family, member 5A (WNT5A), NADPH oxidase 4 (NOX$) and integrin-binding sialoprotein (IBSP). In additional embodiments, the left side prognostic score may include additional genes, such as the gene panel of MMP3, WNT5A, NOX4, IBSP, and SLC16A6, CYPIBI, TFAP2C, MATN3, ANKRD6, to provide a nine gene panel. (See Table 3-LCC panel probes).

The assessment of the expression levels of these genes in a population of left-side colon cancer tumors are naturally divided into high and low components using statistical methods. In the microarray dataset, the low components of MMP3 and WNT5A, and the high components of NOX4 and IBSP, are significantly enriched in left-side colon cancer (LCC) relapse patient specimens. The risk scores of the individual panel genes are computed as the probability that a sample is in the gene's high-risk component, a number between 0 to 1 reported by the statistical method known as mixture modeling. The value of the prognostic score apCL for a given sample is 25 times the sum of the 4 individual gene risk scores. In the validation sets of microarray samples, the 5-year relapse-free survival probabilities in clinically meaningful groups of patients are: 0.92 (95% CI 0.82-1.0 when apCL<25; 0.74 (95% CI 0.53-1.0) when apCL is 25 and <50; 0.34 (95% CI 0.16-0.70) when apCL>50.

Right-Side Colon Cancer—Prognostic Gene Panels:

In some embodiments, the four genes defining the right-side prognostic score, denoted apCR, are family with sequence similarity 69, member A (FAM69A), caudal type homeobox 2 (CDX2), integrin, alpa 3 (antigen CD49C, alpha 3 subunit of VLA-3 receptor) (ITGA3) and family with sequence similarity 84, member A (FAM84A). In additional embodiments, the left side prognostic score may include additional genes, such as a gene panel of 9 genes. By way of example, a nine gene panel for RCC would comprise FAM69A, CDX2, ITGA3, FAM84A, and ITPRIP, RAB3B, SMAD3, PCSK5, and MMP28 (See Table 4—RCC panel probes).

The assessment of the expression levels of these genes in a population of right-side colon cancer tumors are naturally divided into high and low components using statistical methods. In the microarray dataset, the low components of FAM69A, FAM84A and CDX2, and the high components of ITGA3, are significantly enriched in right-side colon cancer (RCC) relapse patient specimens. The value of the prognostic score apCR for a given sample is the number of poor prognosis components in which the sample's expression values are found. In the independent dataset of primary FFPE samples, following translation of the test to RT-PCR, the five-year probability of relapse-free survival for samples with apCR=0 is 0.93 (95% CI 0.80-1), and the corresponding probability for samples with apCR greater than 1 is 0.42 (95% CI 0.21-0.81).

Kits:

The present invention also provides for medical kits useful in LCC and/or RCC disease stratification. In some embodiments, the kit will include reagents useful, sufficient, or necessary for detecting and/or characterizing the level of a right-side colon cancer disease gene expression panel, a left-side colon cancer disease gene expression panel, or both. The kit will also include a means for detecting the expression of the biomarkers of a right-side colon cancer disease comprising FAM69A, CDX2, FAM84A and ITGA3, biomarkers of a left-side colon cancer disease comprising NOX4, WNT5A, MMP3, and a IBSP, or both, as well as a control gene YWHAZ expression profile. The kit should also include instructions on how to use the kit. In some embodiments, the biomarkers of the kit will be provided on a microchip. A computer program, also part of the kit, will calculate apCR from the gene expression measurements of the right-side panel genes and the control gene, and will calculate apCR from the gene expression measurements of the right-side panel genes and the control gene. The program may be provided, for example, by including a disc or other down-loadable form of the computer program, for use by the technician, laboratory, or other laboratory and/or reference technical assistant or clinician.

Primer/Probe Sets:

The present invention also provides for a specific library of prognostic probes for LCC disease (Table 3) and RCC disease (Table 4). In addition, a library of RT-PCR primer sequences is disclosed (Table 6). These materials are particularly efficacious in the practice of the herein described stratification methods, kits, and clinical management tools.

Computer Related Embodiments:

The present invention also provides a variety of computer-related embodiments. In some embodiments the invention provides computer programming for analyzing and comparing a pattern of LCC or RCC gene expression patterns for assessing risk of relapse, using apCL and apCR, employing a colon cancer tissue sample (fresh-frozen or FFPE).

Microchip

The present invention also provides for a microchip useful for assessing risk of colon cancer relapse in a RCC and/or LCC patient. In some embodiments, the microchip may comprise a solid-support suitable for disposition of an oligonucleotide thereon, a set of probes for a right side colon cancer (RCC) biomarker gene panel comprising 4 to 9 genes, said RCC panel comprising a labeled oligonucleotide specific for detecting a FAM69A, CDX2, and a FAM84A gene and/or a set of probes for a left side colon cancer (LCC) biomarker gene panel comprising 4 to 9 genes, said LCC panel comprising a labeled oligonucleotide specific for detecting a NOX4, WNT5A, MMP3, and a IBSP gene; a set of primers; and an oligonucleotide corresponding to an endogenous colon cancer control gene YWHAZ.

Combined LCC/RCC Test/Method

In some embodiments, a colon cancer test that proves a 3 stratification system is provided. This test/method is suitable for assessing a treatment plan for a colon cancer patient having a right side colon cancer (RCC) or a left-side colon cancer (LCC), is provided. In some embodiments, the test comprises obtaining a right side colon cancer (RCC) specimen or a left side colon cancer (LCC) specimen, and performing the following steps: where the patient specimen is a right side colon cancer (RCC) specimen, measuring expression levels of an RCC panel of 4 to 9 genes that include a gene FAM69A, CDX2, FAM84A and ITGA3 in the patient colon cancer specimen to provide a patient specimen RCC test gene expression level for each of the RCC panel of genes; normalizing each patient specimen RCC test gene expression level against a control gene expression level of an endogenous control gene for colon cancer (YWHAZ gene) to provide a normalized apCR score for each of the RCC test panel genes; calculating an overall apCR patient score from the normalized individual panel gene apCR scores, and scaling the overall apCR patient score to provide a patient continuous risk score (apCR) of from 0 to 100; administering an aggressive post-surgical adjuvant chemotherapy treatment to the RCC patient where the patient continuous risk score (apCR) indicates a higher risk of relapse (continuous risk score apCR 50 to 100), or not administering an aggressive post-surgical adjuvant chemotherapy treatment to the RCC patient where the patient continuous risk score indicates a lower risk of relapse (continuous risk score apCR 0 to less than 25), or screening the LCC patient having a moderate risk of relapse score (continuous risk score apCL 25 to less than 50) for additional cancer risk factors or chemotherapy sensitivities.

Where the colon cancer specimen is a left side colon cancer (LCC) specimen, the test method may comprise measuring gene expression levels of an LCC panel of 4 to 9 genes that include a MMP3, WINT5A, NOX4, and IBSP gene in the patient colon cancer specimen to provide a LCC test gene level for each of the LCC panel of genes; normalizing each patient specimen LCC test gene expression level against a control gene expression level of an endogenous control gene for colon cancer (YWHAZ) to provide a normalized apCL score for each one of the LCC test panel genes; calculating an overall apCL patient score from the normalized individual panel gene apCL scores, and scaling the overall apCL patient score to provide a patient continuous risk score (apCL) of from 1 to 100; and administering an aggressive post-surgical adjuvant chemotherapy treatment to the LCC patient where the patient continuous risk score (apCL) indicates a higher risk of relapse (continuous risk score apCL 50 to 100), or not administering an aggressive post-surgical adjuvant chemotherapy treatment to the LCC patient where the patient continuous risk score indicates a lower risk of relapse (continuous risk score apCL 0 to less than 25), or screening the LCC patient having a moderate risk of relapse score (continuous risk score apCL 25 to less than 50) for additional cancer risk factors or chemotherapy sensitivities.

In some embodiments, a colon cancer test that proves a 4 stratification system is provided. In one embodiment of the method, the colon cancer test may be described as suitable for assessing a treatment plan for a colon cancer patient having a right side colon cancer (RCC) or a left-side colon cancer (LCC), said test comprising:obtaining a right side colon cancer (RCC) specimen or a left side colon cancer (LCC) specimen, and performing the following steps: where the patient specimen is a right side colon cancer (RCC) specimen, measuring expression levels of an RCC panel of 4 to 9 genes that include a gene FAM69A, CDX2, FAM84A and ITGA3 in the patient colon cancer specimen to provide a patient specimen RCC test gene expression level for each of the RCC panel of genes; normalizing each patient specimen RCC test gene expression level against a control gene expression level of an endogenous control gene for colon cancer (YWHAZ gene) to provide a normalized apCR score for each of the RCC test panel genes; calculating an overall apCR patient score from the normalized individual panel gene apCR scores, and scaling the overall apCR patient score to provide a patient continuous risk score (apCR) of from 0 to 100; administering an aggressive post-surgical adjuvant chemotherapy treatment to the RCC patient where the patient continuous risk score (apCR) indicates a very high risk of relapse (continuous risk score apCR 75 to 100), administering a moderately aggressive post-surgical adjuvant chemotherapy treatment to the RCC patient where the patient continuous risk score indicates a relatively high risk of relapse (continuous risk score apCR 50 to less than 75), administering a moderate post-surgical adjuvant chemotherapy treatment to the RCC patient having a fair risk of relapse (continuous risk score apCR 25 to less than 50) or not administering post-surgical adjuvant chemotherapy treatment to the RCC patient having a low risk of relapse (continuous risk score of 0 to less than 25).

Where the colon cancer specimen is a left side colon cancer (LCC) specimen, this method may further comprise measuring gene expression levels of an LCC panel of 4 to 9 genes that include a MMP3, WINT5A, NOX4, and IBSP gene in the patient colon cancer specimen to provide a LCC test gene level for each of the LCC panel of genes; normalizing each patient specimen LCC test gene expression level against a control gene expression level of an endogenous control gene for colon cancer (YWHAZ) to provide a normalized apCL score for each one of the LCC test panel genes; calculating an overall apCL patient score from the normalized individual panel gene apCL scores, and scaling the overall apCL patient score to provide a patient continuous risk score (apCL) of from 0 to 100; and administering an aggressive post-surgical adjuvant chemotherapy treatment to the LCC patient where the patient continuous risk score (apCL) indicates a very high risk of relapse (continuous risk score apCL 75 to 100), administering a moderately aggressive post-surgical adjuvant chemotherapy treatment to the LCC patient having a fair risk of relapse (continuous risk score apCL 50 to less than 75), administering moderate post-surgical adjuvant chemotherapy treatment to the LCC patient having a fair risk of relapse (continuous risk score apCL 25 to less than 50) or not administering post-surgical adjuvant chemotherapy to the LCC patient where the patient continuous risk score indicates a low risk of relapse (continuous risk score apCL 0 to less than 25).

BRIEF DESCRIPTION OF THE FIGURES

FIG. 3 Kaplan-Meier survival plots in the microarray validation set for a discrete version of (a) apCL and (b) apCR. The samples in the right-side and left-side datasets were each divided into three groups by the thresholds 25 and 50. In the right-side case, 69% of samples have apCR<25, 12% have score between 25 and 50, and 19% have score greater than 50. In the left-side case, 48% of samples have apCR<25, 26% have score between 25 and 50, and 26% have score greater than 50. The p-values report the significance of Cox proportional hazard models using the discrete variables.

FIG. 4 Kaplan-Meier survival plots in the microarray validation set for a discrete version of apCL in (a) Dukes' B samples and (b) Dukes' C samples. (a) In Dukes' B, 57% of samples have apCL score <25 with no relapse cases; 27% have apCL between 25 and 50 with 5-year relapse-free survival probability 0.86 (95% CI 0.63-1.0); and 17% have score greater than 50 with 5-year relapse-free survival probability 0.17 (95% CI 0.03-0.997). (b) In Dukes' C, 27.5% of samples have apCL score <25 with 5-year relapse-free survival probability 0.80 (95% CI 0.58-1); 25% have apCL between 25 and 50 with 5-year relapse-free survival probability 0.70 (95% CI 0.47-1.0); and 47.5% have score greater than 50 with 5-year relapse-free survival probability 0.17 (95% CI 0.19-0.70).

FIG. 5 Kaplan-Meier survival plots in the microarray validation set for a discrete version of apCR in (a) Dukes' B samples and (b) Dukes' C samples. (a) In Dukes' B, 73% of samples have apCR score <25 with no relapse cases; 11% have apCL between 25 and 50 with 5-year relapse-free survival probability 0.53 (95% CI 0.21-1.0); and 16% have score greater than 50 with 5-year relapse-free survival probability 0.57 (95% CI 0.24-0.997). (b)) In Dukes' C, 56% of samples have apCL score <25 with 5-year relapse-free survival probability 0.80 (95% CI 0.64-1); 24% have apCL between 25 and 50 with 5-year relapse-free survival probability 0.58 (95% CI 0.30-1.0); and 18% have score greater than 50 with 5-year relapse-free survival probability 0.19 (95% CI 0.04-0.98).

DETAILED DESCRIPTION OF THE PREFERRED EMBODIMENTS

Figure 1A:
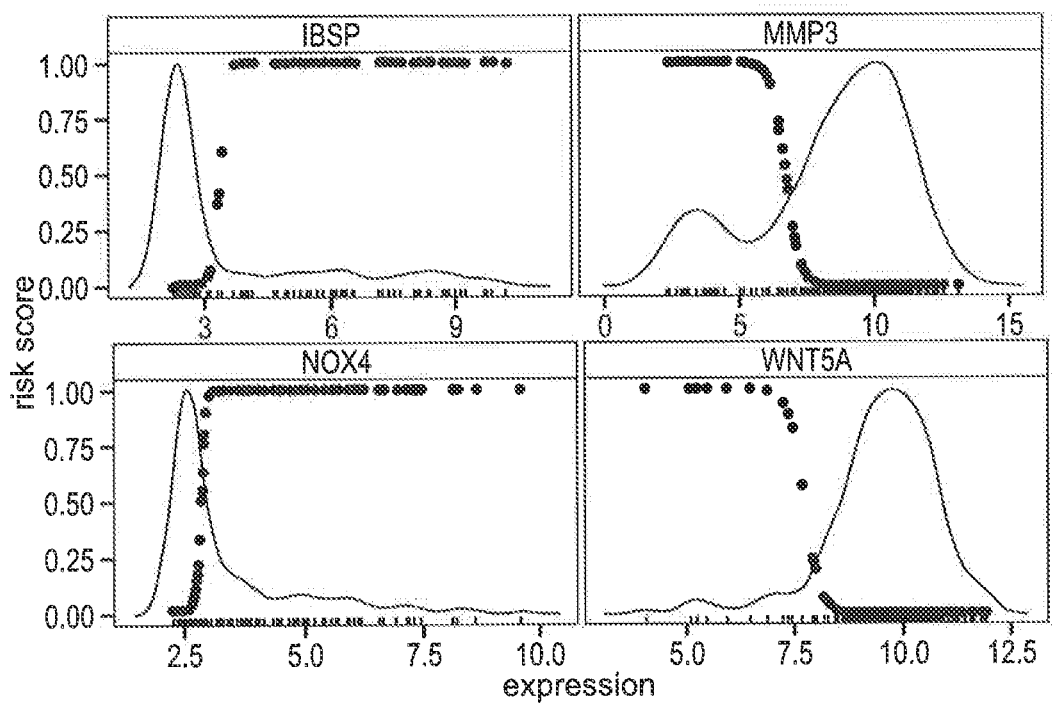
FIG. 1 Plots the gene risk score versus the expression values in the discovery microarray dataset for (a) the left-side panel genes and (b) the right-side panel genes. The density distribution of the expression values, scaled to a range of 0-1, is superimposed on the graph. A Gaussian mixture model was fit to the distribution, separating the expression values into a high component and a low component. The selection algorithm focused on genes for which one of these components is enriched with relapse cases. The risk score is the probability that an expression value is in the high risk component in the mixture model.

Definitions:

One skilled in the art will recognize many methods and materials similar or equivalent to those described herein, which could be used in the practice of the present invention. Indeed, the present invention is in no way limited to the methods and materials described. Singleton, et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application. To further facilitate an understanding of the present invention, a number of terms and phrases are defined definitions as well as several detailed examples are provided below:

As used in the specification and claims, the singular form "a", an and the include plural references unless the context clearly dictates otherwise. For example, the term "a cell" includes a plurality of cells, including mixtures thereof.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about." It also is to be understood, although not always explicitly stated, that the reagents described herein are merely exemplary and that equivalents of such are known in the art.

The term "sample material" is also designated as "sample" of as "specimen" such as a tissue specimen that is fresh frozen, preserved (i.e., FFPE), or otherwise provided in a preserved or semi-preserved state.

The term "biomarker" is meant to designate a protein or protein fragment or a nucleic acid which is indicative for the incidence of the colorectal adenoma and/or colorectal carcinoma. That means the "biomarker" is used as a mean for detecting colorectal adenoma and/or colorectal carcinoma.

As used in the description of the present invention, "p" is defined as a microarray probe for a defined gene expression product. As used in the description of the present invention, a "multi-state gene" is defined as a gene capable of differential levels of expression within a LCC or RCC disease patient population such that the expression levels of the gene in the LCC or RCC disease patient population permits the patient population to be divided into at least two or more distribution groups based on density distribution according to statistical analysis of the levels, such as the expression level of a panel of LCC-associated informative genes (such as NOX4, IBSP, MMP3, WINT5A, SLC16A6, CYPIB1, TFAP2C, MATN3) or RCC associated informative genes (such as CDX2, FAM69A, ITGA3, ITPRIP, FAM84A, RAB3B, SMAD3, PCSK5, MMP28), or oligonucleotides capable of detecting or providing for the quantitation of the gene, such as a specific oligonucleotide panel. For example, the expression levels are divided into two groups based on a mixture model fit of expression levels of the gene of interest. If the density distribution of gene expression for a particular gene of interest can be partitioned into at least two components, a large normal component of expression values below a threshold c, and a long right tail with expression values above c, the gene is a multi-state gene. Alternatively, a gene is multi-state if the density distribution of gene expression for a particular gene of interest is partitioned into at least two components, a large normal component of expression values above a threshold c, and a long left tail with expression values below c.

Mixture Models. Given a numeric vector, the statistical method of finite mixture models partitions the vector into components, each of which is modeled by a different density distribution. The mixture models used to develop the methods described herein fit a pair of gaussian distributions to a vector. Such a model is described by a partition of the vector into components C 1, C2, and a pair of gaussian distributions g 1, g2 modeling the distributions of C1, C2, respectively. The modeling process simultaneously partitions the vector and selects the means, $\mu 1$, $\mu 2$ and standard deviations .sigma.1, .sigma.2 of the two gaussian distributions, with the goal of giving the best possible fit over all alternatives. The fitting algorithm actually produces, for each point and component, a posterior probability that the point is in that component. The point is assigned to the component whose associated posterior probability is maximal. For a point p that is well-classified in, say, component 1, the posterior probability that p is in C2 will be very small. For convenience, posterior probabilities below a threshold A are reported as 0. Following Leisch 2004, we use $\Delta=10-4$. Points that are on the boundary between the two components will have posterior probability $>\Delta$ for both components. The "isolatedness" of, e.g., component 1 is assessed by the ratio, r1=n1/m1, where n1 is the size of C1 and m1 is the number of elements with posterior probability of belonging to C1 greater than $\Delta$. Ratios are .ltoreq.1, with numbers close to 1 representing well-isolated components. Ratios are used to measure the ability of a mixture model fit to describe distinct states.

In most instances, the components defined by a fit of a pair of gaussian distributions consist of a pair of unbroken intervals. That is, there is a cutoff c so that one component consists of the values <c and the other component the values greater than or equal to c. In this way, mixture models can be used to calculate a threshold for dividing a vector into high and low components.

A standard measure of the quality of a mixture model fit is the likelihood, which is the product, over all points, of the maximal posterior probabilities. The likelihood can be used to decide, for example, if a fit with a pair of gaussian distributions is better than a fit with a single gaussian, or if a fit with Gamma distributions is better than a fit with gaussian distributions. Even better measures are AIC and BIC which adjust likelihood by the degrees of freedom. These measures play a part in defining the notion of a multi-state probe. According to one embodiment of this invention, mixture models were fit using the flexmix R package (Leisch, 2004).

"Probe" means a polynucleotide molecule capable of hybridizing to a target polynucleotide molecule. For example, the probe could be DNA, cDNA, cDNA, RNA, cRNA or mRNA. In one embodiment, a probe is fixed, for example, by a covalent bond, to a solid state apparatus such as a microarray. The probe and the target may hybridize, for example, under stringent, or moderately stringent conditions. A probe may be labeled, for example, with a fluorescent or radiolabel to permit identification. In one embodiment, a probe is of a sufficient number of base pairs such that it has the requisite identity to bind uniquely with the target and not with other polynucleotide sequences such that the binding between the target and the probe provides a statistically significant level of accurate identification of the target molecule. In one embodiment, a probe's ability to bind a target is correlated to a statically significant prognostic indicator of a defined disease state as determinable using an identified panel of genes of interest. In one embodiment, the target is mRNA or cRNA and the probe is a complementary piece of DNA or cDNA. In another embodiment, the target is DNA and the probe is a complementary piece of mRNA. In another embodiment, the target is cDNA or DNA and the probe is a complementary piece of DNA (cDNA).

The term "multi-state probe" is meant, in one embodiment, as a probe capable of hybridizing with a target polynucleotide molecule encoding a LCC or RCC specific multi-state gene. In another embodiment, a "multi-state LCC or RCC probe" means a probe capable of hybridizing with a target polynucleotide molecule encoding a relevant portion or fragment of a LCC or RRC multi-state gene, respectively. For example, the target polynucleotide molecule may be mRNA, cRNA or cDNA.

In one embodiment, a LCC or RCC multi-state probe (see Tables 3, 4 and 6, respectively) is fixed to a solid state apparatus such as a microarray by, for example, a covalent bond. In one embodiment, hybridization between the probe and the target occurs under stringent conditions.

The term "hybridize" or "hybridizing" or "hybridization" refers to the formation of double stranded nucleic acid molecule between complementary sequences by way of Watson-Crick base-pairing. Hybridization can occur at various levels of stringency according to the invention. "Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel, et al., Current Protocols in Molecular Biology, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/ 0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2.×SSC (sodium chloride/sodium citrate) and 50% formamide at 55° C., followed by a high -stringency wash consisting of 0.1×.SSC containing EDTA at 55° C. "Moderately stringent conditions" may be identified as described by Sambrook, et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×.SSC at about 37-50° C. The skilled artisan will recognize how to adjust the temperature, ionic strength, etc., as necessary to accommodate factors such as probe length and the like.

The term "microarray" refers to an ordered arrangement of hybridisable array elements, preferably polynucleotide probes, on a substrate.

The terms "differentially expressed gene," "differential gene expression," and their synonyms, which are used interchangeably, refer to a gene whose expression is activated to a higher or lower level in a subject suffering from a LCC or RCC disease, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between normal subjects and subjects suffering from a disease, specifically cancer, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is at least an about two-fold, preferably at least about four-fold, more preferably at least about six-fold, most preferably at least about ten-fold difference between the expression of a given gene in normal and diseased subjects, or between various stages of disease development in a diseased subject.

The term "over-expression" with regard to an RNA transcript is used to refer to the level of the transcript determined by normalization to the level of reference mRNAs, which might be all measured transcripts in the specimen or a particular reference set of mRNAs.

The term "prognosis" is used herein to refer to the prediction of the likelihood of LCC or RCC cancer-attributable death or progression, including recurrence, metastatic spread, and drug resistance, of a neoplastic disease, such as RCC or LCC disease.

The term "prediction" is used herein to refer to the likelihood that a patient will respond either favorably or unfavorably to a drug or set of drugs, and also the extent of those responses, or that a patient will survive, following surgical removal or the primary LCC or RCC tumor and/or chemotherapy for a certain period of time without cancer recurrence. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen, such as surgical intervention, chemotherapy with a given drug or drug combination, and/or radiation therapy, or whether long-term survival of the patient, following surgery and/or termination of chemotherapy or other treatment modalities is likely.

The term "long-term" survival is used herein to refer to survival for at least 5 years according to one preferred embodiment, at least 8 years according to another embodiment, and at least 10 years according to another embodiment, following surgery or other treatment.

The term "tumor," as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, pre-malignancy, malignancy, invasion of surrounding or distant tissues or organs, such as lymph nodes, etc.

The term "at least one," "at least two," "at least five," etc., of the genes listed in any particular gene set means any one or any and all combinations of the genes listed.

The term "node negative" cancer, such as "node negative" colon cancer, is used herein to refer to cancer that has not spread to the lymph nodes.

The term "gcrma" refers to a method known to those of skill in the art whereby raw data obtained from an Affymetrix® microarray is normalized.

"Normalization" refers to statistical normalization. For example, according to one embodiment, a normalization algorithm is the process that translates the raw data for a set of microarrays into measure of concentration in each sample. A survey of methods for normalization is found in Gentleman, et al. For example, a microarray chip assesses the amount of mRNA in a sample for each of tens of thousands of genes. The total amount of mRNA depends both on how large the sample is and how aggressively the gene is being expressed. To compare the relative aggressiveness of a gene across multiple samples requires establishing a common baseline across the samples. Normalization allows one, for example, to measure concentrations of mRNA rather than merely raw amounts of mRNA.

"Biologically homogeneous" refers to the distribution of an identifiable protein, nucleic acid, gene or genes, the expression product(s) of those genes, or any other biologically informative molecule such as a nucleic acid (DNA, RNA, mRNA, iRNA, cRNA, cDNA, etc.), protein, metabolic byproduct, enzyme, mineral, etc., of interest that provides a statically significant identifiable population or populations that maybe correlated with an identifiable disease state of interest.

"Low expression," or "low expression level(s)," "relatively low expression," or "lower expression level(s)" and synonyms thereof, according to one embodiment of the invention, refers to expression levels, that based on a mixture model fit of density distribution of expression levels for a particular multi-state gene of interest falls below a threshold c, whereas "high expression," "relatively high," "high expression level(s)" or "higher expression level(s)" refers to expression levels failing above a threshold c in the density distribution. The threshold c is the value that separates the two components or modes of the mixture model fit.

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", 2nd edition (Sambrook, et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", 4th edition (D. M. Weir & C. C. Blackwell, eds., Blackwell Science Inc., 1987); "Gene Transfer Vectors for Mammalian Cells" (J. M. Miller & M. P. Calos, eds., 4th edition); "Current Protocols in Molecular Biology" (F. M. Ausubel, et al., eds., 1987); and "PCR: The Polymerase Chain Reaction", (Mullis, et al., eds., 1994). The term "individual" or "individuals" is meant to designate a mammal. Preferably, the mammal is a human being such as a patient.

The term "healthy individual" or "healthy individuals" is meant to designate individual(s) not diseased of colorectal adenoma and/or colorectal carcinoma. That is to say, the term "healthy individual(s)" is used only in respect of the pathological condition of colorectal adenoma and/or colorectal carcinoma and does not exclude the individual to suffer from diseases other than colorectal adenoma and/or colorectal carcinoma.

The term "derivative thereof" is meant to describe any modification on DNA, mRNA or protein level comprising, e.g., the truncated gene, fragments of said gene, a mutated gene, or modified gene. The term "gene" includes nucleic acid sequences, such as DNA, RNA, mRNA or protein sequences or oligopeptide sequences or peptide sequences. The derivative can be a modification which is an result of a deletion, substitution or insertion of the gene. The gene modification can be a result of the naturally occurring gene variability. The term "naturally occurring gene variability" means modifications which are not a result of genetic engineering. The gene modification can be a result of the processing of the gene or gene product within the body and/or a degradation product. The modification on protein level can be due to enzymatic or chemical modification within the body. For example the modification can be a glycosylation or phosphorylation or farnesylation. Preferably, the derivative codes for or comprises at least 5 amino acids, more preferably 10 amino acids, most preferably 20 amino acids of the unmodified protein. In one embodiment the derivative codes for at least one epitope of the respective protein.

The term "patient" as used in the present application covers humans as well as non-human beings such as animals. The animals are preferably selected from the group consisting of rodents, e.g., mouse, rat, hamster, and other animals, e.g., cat, horse, guinea-pig, rabbit, hare, dog, pig and any variety of other companion type animals.

Animals can be used to specifically induce certain disease states, like colorectal adenoma and colorectal carcinoma, for research purposes. The induction of said disease states can, for example, be effected by treatment of the animals, for example, with radioactive or chemical substances known to induce colorectal cancer or colorectal adenoma disease state. The disease states can also be induced using viral transfection systems. It is also possible to use genetically modified animals, in which one or more specific gene function(s) has/have been altered, or knock-out animals such as knock-out mice in which a specific gene function has been deleted.

The term "compound" can be one or more chemical substances, an antibody, protein, peptide, antisense mRNA, small molecular drug, or combinations thereof. The compound can also be replaced by irradiation, e.g., X-ray, or combinations of compounds and radiation can be used.

A good prognosis may be defined as a prognosis in which a patient is determined to be unlikely to benefit from cancer treatment such as chemotherapy or radiation, for example, subsequent to a colon cancer surgical procedure. This may be the case where the expression level of the identified bimodal gene or combination of genes for LCC or RCC disease is negatively correlated with mortality.

A poor prognosis patient is used to define a patient that is likely to benefit from further cancer treatment such as chemotherapy or radiation, for example, subsequent to a colon cancer surgical procedure. This may be the case where the expression level of the identified bimodal gene or combination of genes for LCC or RCC disease is positively correlated with mortality.

The terms "marker" or "biomarker" are used interchangeably herein. A biomarker is a nucleic acid or polypeptide and the presence, absence or differential expression of the nucleic acid or polypeptide is used to determine relative risk of relapse in a LCC and/or RCC patient. For example, FAM69A, CDX2, FAM84A and ITGA3 are biomarkers for RCC disease, and the mRNA expression of these genes (or cRNA, cDNA corresponding thereto) are employed as biomarkers of RCC disease and RCC disease prognosis. Similarly, NOX4, WNT5A, MMP3, and IBSP are biomarkers for LCC disease, and the mRNA expression of these genes (or cRNA, cDNA corresponding thereto) are employed as biomarkers of LCC disease and LCC disease prognosis. The mRNA expression levels of these genes is compared to the expression levels of a control endogenous colon cancer gene as part of the RCC and LCC stratification system described herein. By way of example, a particular control endogenous colon cancer gene used in the practice of the present tests, methods and panels is YWAZ gene. The mRNA expression levels of these genes is comparable to the expression levels of a control endogenous colon cancer gene as part of the RCC and LCC stratification methods/panels/systems described herein. Thus, the values provided are relative, not absolute, quantification ratios.

The term "stratification" refers to the partition of a set of patients or tissue samples into a finite number of groups that are ordered according to some criterion, for example, the risk of relapse or the effectiveness of a drug in this invention.

The term "adjuvant chemotherapy" refers to drug treatment given post-surgical resection of the tumor to reduce the likelihood of relapse.

The term "strata" refers to the groupings of patients defined by a stratification. The term "stratum" refers to one of the groups.

The term "gene" refers to a nucleic acid (e.g., DNA) sequence that comprises coding sequences necessary for the production of a polypeptide, RNA (e.g., including but not limited to, mRNA, tRNA, cRNA and rRNA) or precursor. The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

A "probe" when used in the context of polynucleotide manipulation refers to an oligonucleotide that is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to radioisotopes, fluorochromes, chemiluminescent compounds, dyes, and proteins, including enzymes.

A "primer" is a short polynucleotide, generally with a free 3'-OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in PCR: A Practical Approach, M. MacPherson et al., IRL Press at Oxford University Press (1991). All processes of producing replicate copies of a polynucleotide, such as PCR or gene cloning, are collectively referred to herein as "replication." A primer can also be used as a probe in hybridization reactions, such as Southern or Northern blot analyses (Sambrook et al., Molecular Cloning: A Laboratory Manual, 2nd edition (1989)).

As used herein, "expression" refers to the process by which DNA is transcribed into mRNA and/or the process by which the transcribed mRNA is subsequently translated into peptides, polypeptides or proteins. If the polynucleotide is derived from genomic DNA, expression may include splicing of the mRNA in a eukaryotic cell.

A "gene expression profile" refers to a pattern of expression of at least one biomarker that recurs in multiple samples and reflects a property shared by those samples, such as tissue type, response to a particular treatment, or activation of a particular biological process or pathway in the cells. Furthermore, a gene expression profile differentiates between samples that share that common property and those that do not with better accuracy than would likely be achieved by assigning the samples to the two groups at random. A gene expression profile may be used to predict whether samples of unknown status share that common property or not. Some variation between the levels of at least one biomarker and the typical profile is to be expected, but the overall similarity of the expression levels to the typical profile is such that it is statistically unlikely that the similarity would be observed by chance in samples not sharing the common property that the expression profile reflects.

The term "tag" or "label" is defined as a detectable tag or label, that may be used to detect, monitor, quantify, and otherwise identify the presence or absence of a particular oligonucleotide or specific nucleic acid sequence, and may be used to label or tag a cDNA, cRNA, mRNA, DNA, or any other type of nucleic acid probe or primer. These tags or labels include, by way of example and not limitation, visually detectable labels, such as, e.g., dyes, fluorophores, and radioactive labels, as well as biotin to provide biotinylated species of oligonucleotide, mRNA, cRNA, etc. In addition, the invention contemplates the use of magnetic beads and electron dense substances, such as metals, e.g., gold, as labels. A wide variety of radioactive isotopes may be used including, e.g., $^{14}C$, $^{3}H$, $^{99m}Tc$, $^{123}I$, $^{131}I$, $^{32}P$, $^{192}Ir$, $^{103}Pd$, $^{198}Au$, $^{111}In$, $^{67}Ga$, $^{201}Tl$, $^{153}Sm$, $^{18}F$ and $^{90}Sr$. Other radioisotopes that may be used include, e.g., thallium-201 or technetium 99m. In other embodiments, the detectable agent is a fluorophore, such as, e.g., fluorescein or rhodamine. A variety of biologically compatible fluorophores are commercially available The term "cDNA" refers to complementary DNA, i.e. mRNA molecules present in a cell or organism made into cDNA with an enzyme such as reverse transcriptase. A "cDNA library" is a collection of all of the mRNA molecules present in a cell or organism, all turned into cDNA molecules with the enzyme reverse transcriptase, then inserted into "vectors" (other DNA molecules that can continue to replicate after addition of foreign DNA). Exemplary vectors for libraries include bacteriophage (also known as "phage"), viruses that infect bacteria, for example, lambda phage. The library can then be probed for the specific cDNA (and thus mRNA) of interest.

The term "cRNA" refers to complementary ribonucleic acid, i.e., a synthetic RNA produced by transcription from a specific DNA single stranded template. The cRNA can be labeled with radioactive uracil and then used as a probe. (King & Stansfield, A Dictionary of Genetics, 4th ed). Alternatively, a non-radioactive label, such as biotin or other non-radioactive label, may be used to label the cRNA probe. cRNA is also described as a single-stranded RNA whose base sequence is complementary to specific DNA sequences (e.g., genes) or, more rarely, another single-stranded RNA; usually conveys an artificial hybridization probe or antisense genetic inhibitor.

As an example, transcriptional activity can be assessed by measuring levels of messenger RNA using a gene chip such as the Affymetric.RTM. HG-U133-Plus-2 GENECHIPS. High-throughput, real-time quantitation of RNA of a large number of genes of interest thus becomes possible in a reproducible system.

Particular combinations of markers may be used that show optimal function with different ethnic groups or sex, different geographic distributions, different stages of disease, different degrees of specificity or different degrees of sensitivity. Particular combinations may also be developed which are particularly sensitive to the effect of therapeutic regimens on disease progression. Subjects may be monitored after a therapy and/or course of action to determine the effectiveness of that specific therapy and/or course of action.

The present invention defines an LCC and RCC disease stratification system that employs a patients' individual LCC and RCC gene panel level (such as gene expression level) to determine the individual patients' LCC or RCC disease score, the disease score stratifying the patient into a particular group (very poor to good), that coincides with the patient's risk of LCC or RCC disease relapse. The LCC and RCC disease scores are based on the expression levels of a LCC panel of 4 genes, or of 4 to 9 or 10 genes, and a RCC panel of 4 genes, or of 4 to 9 or 10 genes, that significantly stratifies patients according to risk of relapse.

In particular, the 5-year expected survival probability for the poorest prognosis strata in the FFPE data set are 0.42 (95% CI 0.21-0.81) for LCC and 0.50 (95% CI 0.19-1.0) for RCC. Patients with stage II colon cancer having such poor prognosis may benefit from adjuvant chemotherapy. It is estimated that these strata contain approximately 15% of stage II colon cancer patients; however, they contain the majority patients who will relapse (FIGS. 4, 5a, and Table 7). Thus, aggressive treatment of these relatively few patients may yield a significant reduction in the colon cancer mortality rate. The fact that the test can be implemented with FFPE tissue greatly enhances the applicability of the test for clinical use.

Here, the FFPE data set is used to further validate the choice of genes for apCR and apCL made with the microarray-based discovery set. The form of the test using RT-PCR, most specifically the selection of thresholds between low and high components for the panel genes, will also be validated.

The effect of adjuvant chemotherapy on the stage II colon cancer patients in the strata with the highest apCR and apCL scores is estimated as follows. The microarray dataset contains both Dukes' B and Dukes' C samples. As FIGS. 3 and 4 show, the apCR and apCL tests stratify patients by risk in a similar manner in both of these stages. This correspondence demonstrates the utility for use of this method to identify forms of treatment effective in both stages. Since adjuvant chemotherapy with fluorouracil and folinic acid reduces mortality in stage III colon cancer by 18% [1], a comparable reduction in mortality rate can be expected in stage III patients. The 5-year relapse rate in the poorest prognosis strata defined by apCR and apCL is approximately 0.50, and most of these patients die from the disease (Table 2 and [1]). Thus, the reduction in mortality rates in the highest risk strata, due to adjuvant chemotherapy, is estimated as 9% of the patients in the strata. This contrasts favorably with the observed 3.6% reduction in absolute mortality rate due to chemotherapy in stage II colon cancer overall [1].

Panels of genes were identified that significantly stratify colon cancer patients by risk of relapse. Separate sets of genes were used for right-side colon cancer and left-side colon cancer. The highest risk strata of stage II patients may benefit from the same form of adjuvant chemotherapy used effectively in the treatment of stage III colon cancer. These prognostic tests are demonstrated with RT-PCR using an FFPE tissue source, showing that they are clinically viable.

A medical professional can communicate the assay results to a patient or a patient's family. In some cases, a medical professional can provide a patient and/or a patient's family with information regarding right side colon cancer or left side colon cancer in a patient, including treatment options, prognosis, and referrals to specialists, e.g., oncologists and/or radiologists. In some cases, a medical professional can provide a copy of a patient's medical records to communicate the assay results provided according to the present invention, alone or in combination with other clinical information, to a specialist. A research professional can apply information regarding a subject's assay results to advance colon cancer research. For example, a researcher can compile data on the assay results, with information regarding the efficacy of a drug for treatment of right side colon cancer disease and/or left side colon cancer disease, an effective treatment and/or the most patient compatible treatment. In some cases, a research professional can obtain assay results to evaluate a subject's enrollment, or continued participation in a research study or clinical trial. In some cases, a research professional can classify the severity of a subject's condition, based on assay results. In some cases, a research professional can communicate a subject's assay results to a medical professional. In some cases, a research professional can refer a subject to a medical professional for clinical assessment of the colon cancer (RCC or LCC), and treatment thereof.

Any appropriate method can be used to communicate information to another person (e.g., a professional). For example, information can be given directly or indirectly to a professional, or a laboratory technician can input the assay results into a computer-based record. In some cases, information is communicated by making a physical alteration to medical or research records. For example, a medical professional can make a permanent notation or flag a medical record for communicating a diagnosis to other medical professionals reviewing the record. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

The following examples are provided in order to demonstrate and further illustrate certain preferred embodiments and aspects of the present invention and are not to be construed as limiting the scope thereof.

Example 1

Materials and Methods

Scoring functions are developed from the expression levels of few genes, separately for left-side and right-side colon cancer, that stratify patients by risk of relapse. Microarray data from 102 right-side colon carcinomas and 95 left-side colon carcinomas are used to select the genes used in our prognostic scores. Formalin-fixed and paraffin-embedded (FFPE) samples from an independent set of 44 stage II right-side colon carcinomas and 39 stage II left-side colon carcinomas are used to validate the tests, following translation of the tests to FFPE tissue and real-time polymerase chain reaction (RT-PCR) with representative cell lines.

Microarray Data Set Used as the Discovery Set/Microarray Techniques for RCC and LCC Prognostic Tests The microarray data set used as the discovery set was published in [10] and is publicly available on the Gene Expression Omnibus as GSE14333. The data were generated with AFFYMETRIX array hgu133plus2. The characteristics of the patients used here are reported in Table 1. The survival endpoint used here is any form of relapse, including local relapse, distant metastasis or death due to colon cancer. In this paper, survival data was censored to 5 years, reflecting the duration of the study [10].

In one embodiment, the reference expression data may be generated using a platform selected from the group including cDNA microarrays, oligonucleotide microarrays, protein microarrays, micro RNA (miRNA) arrays, and high-throughput quantitative polymerase chain reaction (qPCR). Microarrays can be produced on any suitable solid support known in the art, the more preferable supports being plastic or glass.

Oligonucleotide microarrays may be used in the present invention. If this type of microarray is used, each molecule being assayed is a polynucleotide, which may either be represented by a single probe on the microarray or by multiple probes, each probe having a different nucleotide sequence corresponding to part of the polynucleotide. If multiple probes are present, one of said analysis programs might include instructions for summarizing the expression levels of the multiple probes into a single expression level for the polynucleotide.

Oligonucleotide microarrays such as those manufactured by AFFYMETRIC, Inc. and marketed under the trademark GENECHIP currently represent the vast majority of microarrays in use for gene (and other nucleotide) expression studies. As such, they represent a standardized platform which particularly lends itself to collation of large databases of expression data, for example from cancer patients, in order to provide a basis for diagnostic or prognostic applications such as those provided by the present invention.

TABLE 1

Characteristics of the LCC and RCC patients in GSE14333

|  | No. | gender (M/F) | Dukes' |  | relapse (no/yes/ NA) | chemo (no/yes) |
|---|---|---|---|---|---|---|
| Left | 122 | 77/45 | A | 18 | 15/1/2 | 16/2 |
|  |  |  | B | 37 | 31/6/0 | 29/8 |
|  |  |  | C | 40 | 22/18/0 | 10/30 |
|  |  |  | D | 27 | — | — |
| Right | 125 | 59/66 | A | 17 | 16/0/1 | 17/0 |
|  |  |  | B | 44 | 40/4/0 | 33/11 |
|  |  |  | C | 41 | 27/14/0 | 13/28 |
|  |  |  | D | 23 | — | — |

Data Set of FFPE Samples Used for Validation and Translation

The samples employed in the present example are from colon cancer patients treated at Elkhart General Hospital, Elkhart, Ind., from 2000 to 2005. These samples have not been presented in any publication. All patients had stage II disease and none received adjuvant chemotherapy. Local relapse, distant metastasis and death from cancer were all recorded. Approval for the present use of these archived samples was received from the Institutional Review Boards of Elkhart General Hospital and the University of Notre Dame. A single 14 µm rolled section was obtained for each patient.

Table 2 reports the characteristics of the patients whose samples are included in this study. In the microarray study the prognostic test derived for left-side samples was not valid in rectal tumors. For this reason we separate the rectal samples from the left-side samples. The median follow-up time for these patients is 72 months. We censored the survival statistics at this time point and counted only local or distant relapse events that occurred by that time. Note that there are 4 patients who died from cancer after 72 months, but did not exhibit a local or distant relapse. Our model is not designed to predict such outcomes, so we censor these cases to the status at 72 months.

TABLE 2

Characteristics of Patients providing FFPE tumor samples

| Characteristic | LCC | RCC |
|---|---|---|
| No. Patients | 39 | 44 |
| Gender (M/F) | 15/24 | 25/19 |
| Median age at resection-years (range) | 75 (38-90) | 75.5 (35-92) |
| Relapse within in 5 years (no/yes) | 28/11 | 35/9 |
| Local relapse | 5 | 3 |
| Distant relapse | 6 | 6 |
| Death from cancer | 11 | 9 |
| Stage |  |  |
| IIA | 39 | 43 |
| IIB |  |  |
| IIC |  | 1 |
| Histologic Grade |  |  |
| G1 | 5 | 3 |
| G2 | 33 | 36 |
| G3 | 1 | 5 |
| Death within 5 years due to other causes (no tumor recurrence) | 1 | 6 |

Example 2

Measurement of mRNA in FFPE Colon Cancer Tissue

The present example demonstrates the utility of the present invention for providing a tool and method useful in the assessment of risk of colon cancer relapse using an FFPE tissue sample from a colon cancer patient.

Common practice in clinical pathology is to preserve a solid tumor tissue sample in formalin and fix it in paraffin, this tissue sample being referred to as an FFPE tissue specimen. This FFPE tissue specimen is examined under a microscope in the process of establishing the tumor state and it is readily available for staining with protein antibodies or analysis of DNA. Translating a genomic prognostic test developed with microarrays and a fresh-frozen tissue sample, to one that uses FFPE tissue, faces several difficulties. One of these difficulties is that fixing tissue in formalin is known to degrade some species of mRNA. Thus, if two samples recovered from the same tissue block, one frozen and one prepared as an FFPE block, are hybridized to whole-genome microarray, some of the mRNA species will produce equivalent readings on both arrays and others will show significantly reduced levels in the sample from FFPE tissue. For this reason, analyses that measure the entire genome of mRNA species, such as microarray analysis with AFFYMETRIC GENECHIP arrays, has required the clinician/technician to obtain and use a frozen tissue sample. However, through the particular methodologies disclosed in the present specification, the ability to use an FFPE block tissue sample, while providing results that are comparable to results achieved using fresh -frozen colon cancer tissues, is provided. With the methods described herein, significantly comparable and even improved, more robust, colon cancer prognostic and stratification data are provided using FFPE block tissue, compared to those data obtained with fresh-frozen tissue samples in a microarray assessment.

The present example demonstrates the utility of the present invention as a widely useable diagnostic tool for FFPE preserved colon tumor samples that is reliable, accurate and highly prognostic in assessing and evaluating risk of colon cancer relapse in the absence of post-surgical resection adjuvant chemotherapy.

The prognostic tests for LCC and RCC disclosed in this invention uses several genes in its several embodiments. A significant increase in prognostic power has not been found with more than about 9 to 12 genes. An efficient method for measuring the expression levels of few genes is quantitative RT-PCR (recerse transcription polymerase chain reaction). Thus, one version of the test for use in a clinical setting will use RT-PCR to measure several species of mRNA from an FFPE tissue source.

Total RNA was extracted from the FFP tissue sections using the RNEASY FFPE kit (Qiagen, Germantown, MD) following the enclosed procedure. The paraffin was removed using Deparaffinization Solution (Qiagen). A DNase treatment was included in the procedure. The RNA concentration for each sample was obtained from $A_{260}$ measurements determined using a Nanodrop 2000 UV-VIS spectrophotometer (Nanodrop, Rockland, DE). In addition, the 260/280 and 260/230 ratios were taken into consideration as a measurement of RNA quality and purity. Complementary DNA (cDNA) was generated from total RNA using the High-Capacity reverse Transcriptase cDNA kit (Applied Biosystems, Foster City, CA) according to the manufacturer's instructions. The following thermal cycler conditions were used: 10 min at 25° C. Quantitative PCR reactions were performed with a real-time PCR system, STEPONEPLUS (Applied Biosystems). Reactions were conducted with 300 ng of cDNA, in a final volume of 25 µL. The PCR mixture contained GOTAQ qPCR Master Mix (Promega, Madison, WI) and 0.nmol of each gene-specific primer (forward and reverse). For each gene, the consensus sequence was accessed through the NCBI nucleotide database.

RT-PCR primers were designed using Primer 3 (v.0.4.0) with amplicon sizes limited to less than 100 bases in length. The specificity of the primers was evaluated with melt curve analysis, to assess the dissociation characteristics of the double stranded DNA and to monitor the number of products detected in each reaction.

Oligonucleotides were supplied from Operon (Huntsville, Ala.) and Sigma-Aldrich (St. Louis, Mo.). Primer sequences are provided in Table 5. PCR cycling was performed as follows: 95° C. for 2 min for one cycle, 95° C. for 15 sec, and 60° C. for 60 sec for 45 cycles followed by a 60-95° C. dissociation cycle. An optimal threshold was set for each gene within the log-linear amplification phase at which the fluorescent signal exceeded the baseline mean. The levels of transcripts ($\Delta CT$), where $\Delta CT=CT$ (gene of interest)–CT (reference gene), were quantified relative to levels of YWHAZ. YWHAZ has been previously identified as a suitable endogenous control gene for colon cancer [11, 12]. All samples were analyzed in triplicate wells with the median of each measurement used for CT calculations.

Example 3

Construction of Multigene Survival Models with a Panel of Multistate Genes

An array probe (gene) is called multistate if the probe's expression values naturally divide samples into two distinct subtypes. For a multistate probe p there is a threshold c, determined by statistical methods, such that the samples with expression values above c, denoted p+, forms the high expression component, and the samples with expression values below c, denoted p–, form the low expression component. Many genes have nearly normal expression distributions, hence are not considered multistate. The formal definition of a multistate gene is found in [9].

In the multistate genes correlated with relapse, one of the components is highly enriched with relapse cases. In prior work, the principle that a multistate probe represents distinct states was exploited, the expression vector for a multistate probe is replaced by a binary variable in which all samples in the poor prognosis component are given the value 1, and all samples in the better prognosis component have the value 0. Here, the significance of a multistate probe in a survival model is measured by the p-value of a Cox proportional hazard model (CPH) using only the probe's binary variable.

In the methodology disclosed herein, in contrast, the multistate methodology previously developed has been revised to produce more powerful continuous risk scores as follows. One weakness of the original methodology is that the uncertainty of the precise value of the threshold between a gene's components results in uncertainty of the prognosis of a sample. Here, deeper mixture model methodology found in (Fraley, C., & Raftery, A. E. (2002). Model-Based Clustering, Discriminant Analysis, and Density Estimation. *Journal of the American Statistical Association,* 97(458), 611-631.) is used to replace the binary classification of sample as good prognosis (value=0) or poor prognosis (value=1) by a probability that the sample has poor prognosis (a number between 0 and 1). Most values of this gene risk score are very close to 0 or 1, however samples near the threshold may have values like 0.1, 0.3, 0.7 or 0.9, for example. A risk score of 0.9, for example, is interpreted as saying that there is a 90% risk the sample is poor prognosis, as measured by this gene.

A prognostic score for a panel of multistate genes is defined as the sum of the risk scores of these genes. This contrasts with the method previously used, in which the multigene prognostic variable is 1 if any of single-gene variables is 1, and 0 otherwise. Advantages of the present method, among others, include the observation that the score increases with the number of panel genes for which the sample is in a high risk state. The results reported herein demonstrate that the prognosis for samples with very high values of the panel risk score is significantly lower than what would be predicted using the previous, original methods.

In some embodiments, the prognostic panel score is normally scaled to values between 0 and 100 for ease of use by clinicians. For example, if there are 4 genes in the panel being used for the RCC panel or LCC panel genes as defined herein, the risk scores for the individual genes are designated r1, r2, r3 and r4, where each risk score is a vector of numbers between 0 and 1. The panel risk score is then multiplied by 25 in the case of four genes being used in the panel (the number 25 is obtained by dividing 100 by the number of genes in the panel being used). In the present example, 4 genes are in the panel. (If 9 genes were being used in the panel, then the multiplier 11 would be used (100 divided by 9 is approximately 11, 10.9); 5 gene panel, the multiplier is 20; 6 gene panel, the multiplier is approximately 17 (16.67), 7 gene panel, the multiplier is approximately 14 (14.2); 8 gene panel, the multiplier is approximately 12 (12.5)). Thus, in the present example, the score of the patient is made by multiplying 25 by the sum of the risk scores determined for the first gene (r1), the risk score determined for the second gene (r2), the risk score determined for the third gene (r3) and the risk score determined for the fourth gene (r4). The result of this calculation provides a value between 0 and 100, which is then used as the individual's continuous risk score. The attending physician may then take this patient risk score and compare it against a reference table/chart. For example, in some embodiments, a three-group stratification system is provided, and provides a range of patient risk score values that define a "very poor" (score of 50 to 100), "poor" (score of 25 to less than 50), or "good" (score of 0 to less than 25) relapse free group. The attending physician/clinician and patient may, for example, employ this information on risk of relapse-free survival for colon cancer score and classification, to design a treatment regimen most appropriate to the patient. The individual's patient panel score, in addition or alternatively, may be stratified against a reference chart that includes a stratification system of 4 groups, a very poor relapse free (75 to 100) group, a poor relapse-free (50 to less than 75) group, a fair relapse-free (25 to less than 75) group and a good relapse-free (0 to less than 25) group. By way of example, a reference chart for the 3 Group-stratification system and the 4 Group-stratification system appear below:

Three Group Stratification System Chart:

| Left-Side Colon Cancer | | | Right-Side Colon Cancer | | |
|---|---|---|---|---|---|
| apCL score | Prognosis | Treatment recommended | apCR score | Prognosis | Treatment recommended |
| 0-24 | Good | No chemotherapy | 0-24 | Good | No chemotherapy |
| 25-49 | Fair | Further Testing for Risk Factors | 25-49 | Fair | Further Testing for Risk Factors |
| 50-100 | Poor | Administer Chemotherapy | 50-100 | Poor | Administer Chemotherapy |

Four Group Stratification System Chart:

| Left-Side Colon Cancer | | | Right-Side Colon Cancer | | |
|---|---|---|---|---|---|
| apCL score | Prognosis | Treatment recommended | apCR score | Prognosis | Treatment recommended |
| 0-24 | Good | No chemotherapy | 0-24 | Good | No chemotherapy |
| 25-49 | Fair | Further Testing for Risk Factors | 25-49 | Fair | Further Testing for Risk Factors |
| 50-75 | Poor | Administer Chemotherapy | 50-100 | Poor | Administer Chemotherapy |
| 75-100 | Very poor | Administer Most Aggressive Chemotherapy | 75-100 | Very poor | Administer Most Aggressive Chemotherapy |

Following the derivation of gene risk scores in a discovery set of samples, the risk scores can be defined in another set of samples (a validation set) using statistical methods for extending mixture model fits to a new set of samples (Fraley, C., & Raftery, A. E. (2002). Model-Based Clustering, Discriminant Analysis, and Density Estimation. *Journal of the American Statistical Association*, 97(458), 611-631.) Construction of discrete risk strata from a continuous panel risk score:

A continuous risk score has the advantage of accurately measuring a patient's true risk of relapse. However, clinical treatment decisions are discrete events; a patient is recommended for receiving chemotherapy, or not. To help support clinical decisions, the patient population may be divided into ordered risk groups (also known as strata) defined by intervals of the risk score. For example, For example, the patients could be separated into 4 risk groups: (1) lowest risk patients with score <25, (2) moderate risk group with score between 25 and 50, (3) high risk group with score between 50 and 75, and (4) very high risk group with score greater than 75. Conceivably, different treatment plans would be chosen for each group.

Statistical Analysis:

A variable's influence on relapse will be assessed with a Cox proportional hazard model (CPH). A CPH model is considered statistically significant if the p-value of the logrank test is less than 0.05. This is the p-value that we associate with all survival models herein. All statistical analyses were performed with R versions 2.15.0 and 3.02. Figures were generated with the ggplot2 package [13].

Example 4

Procedure for the Discovery and Validation of the apCL and apCR Prognostic Scores in the Microarray Dataset The present example describes the discovery and validation process followed for the prognostic panel disclosed herein and outlined as follows
1. A large set of candidate genes was used identified from statistical analysis of risk in the full sets of LCC and RCC cases;
2. A discovery set of microarray samples was used to identify (a) the mixture model fits for the candidate genes and the resulting individual gene risk scores and (b) the specific genes forming the panels defining apCL and apCR, selected from among the candidate genes;
3. Given an independent validation set of microarray samples, the mixture model fits for the panel genes are extended from the discovery set to the validation set (see methods Example 2), the individual gene risk scores are computed and the apCL and apCR panel risk scores computed;
4. Show that apCL and apCR are statistically significant predictors of relapse in the left-side and right-side validation sets, respectively Selection of the Discovery Sample Set:

The prognostic score employed in the present invention was derived using the microarray dataset GSE14333. The characteristics of the patients in this cohort are found in Table 1. Here, samples with Dukes' A, B or C and any chemotherapy treatment status were used. Subsets of the right-side samples and the left-side samples consisting of ⅓ of the total numbers were randomly selected as the LCC and RCC discovery sets. Selection of candidate genes for the Right side and left side Colon Cancer Tests:

The first step in building a multi-gene prognostic panel is to select a relatively small set of candidate genes based on properties of the individual genes. The following steps are for the LCC case. The steps for the RCC case will follow the same methodology. Here, the set S of 95 LCC cases with Dukes' A, B or C is used.
1. For each probe, calculate a CPH model with the expression values of that probe as the only variable. Restrict attention to the 100 most significant probes as determined by the p-value of the logrank score of these CPH models.
2. Identify the multistate probes in this set of 100 and form a database of binary variables representing the high and low components. The algorithm identifies 51 multistate probes;
3. Form a set T of 100 subsets of S, each consisting of ⅔ of the samples and balanced for relapse events. For each binary variable v defined in 2, and each set in T, compute the p-value of the logrank score of a CPH model whose only variable is v. Rank order the binary variables by the median p-values ranging over all sets in T.
4. Select some number of the top ranked probes from 3 (corresponding to the binary variables) as candidate probes for the prognostic score.

Tables 3 and 4 contain the top 9 multistate probes to be used for each of the LCC (Table 3) and RCC (Table 4) disease conditions, respectively. Experience has shown that multi-gene tests that are derived by this method and generalize well to a larger population rarely contain more than 4 or 5 genes. Using many more genes than this number risks over-fitting the data. Thus, the choice of 9 probes for each of the LCC and RCC disease assessment provides at least one of the preferred embodiments of the prognostic probe sets of the present invention.

TABLE 3

Prognostic probes for left-side colon cancer (LCC):

| Probe | Symbol | Name | ACCN | Poor prognosis component |
|---|---|---|---|---|
| 205828_at | MMP3 | matrix metallopeptidase 3 (stromelysin 1, progelatinase) | NM_002422 | LOW |
| 230748_at | SLC16A6 | solute carrier family 16, member 6 (monocarboxylic acid transporter 7) | AI873273 | HIGH |
| 205990_s_at | WNT5A | wingless-type MMTV integration site family, member 5A | NM_003392 | LOW |
| 202435_s_at | CYP1B1 | cytochrome P450, family 1, subfamily B, polypeptide 1 | AU154504 | HIGH |
| 219773_at | NOX4 | NADPH oxidase 4 | NM_016931 | HIGH |
| 236028_at | IBSP | integrin-binding sialoprotein | BE466675 | HIGH |
| 205286_at | TFAP2C | transcription factor AP-2 gamma (activating enhancer binding protein 2 gamma) | U85658 | HIGH |
| 206091_at | MATN3 | matrilin 3 | NM_002381 | HIGH |
| 204672_s_at | ANKRD6 | ankyrin repeat domain 6 | NM_014942 | HIGH |

TABLE 4

Prognostic probes for right-side colon cancer (RCC):

| Probe | Symbol | Name | ACCN | Poor prognosis component |
|---|---|---|---|---|
| 216044_x_at | FAM69A | family with sequence similarity 69, member A | AK027146 | LOW |
| 206387_at | CDX2 | caudal type homeobox 2 | U51096 | LOW |
| 225582_at | ITPRIP | inositol 1,4,5-trisphosphate receptor interacting protein | AA425726 | HIGH |
| 201474_s_at | ITGA3 | integrin, alpha 3 (antigen CD49C, alpha 3 subunit of VLA-3 receptor) | NM_002204 | HIGH |
| 225667_s_at | FAM84A | family with sequence similarity 84, member A | AI601101 | LOW |
| 227123_at | RAB3B | member RAS oncogene family | AU156710 | HIGH |
| 218284_at | SMAD3 | SMAD family member 3 | NM_015400 | HIGH |
| 205559_s_at | PCSK5 | proprotein convertase subtilisin/kexin type 5 | NM_006200 | HIGH |
| 219909_at | MMP28 | matrix metallopeptidase 28 | NM_024302 | HIGH |

Figure 1B:
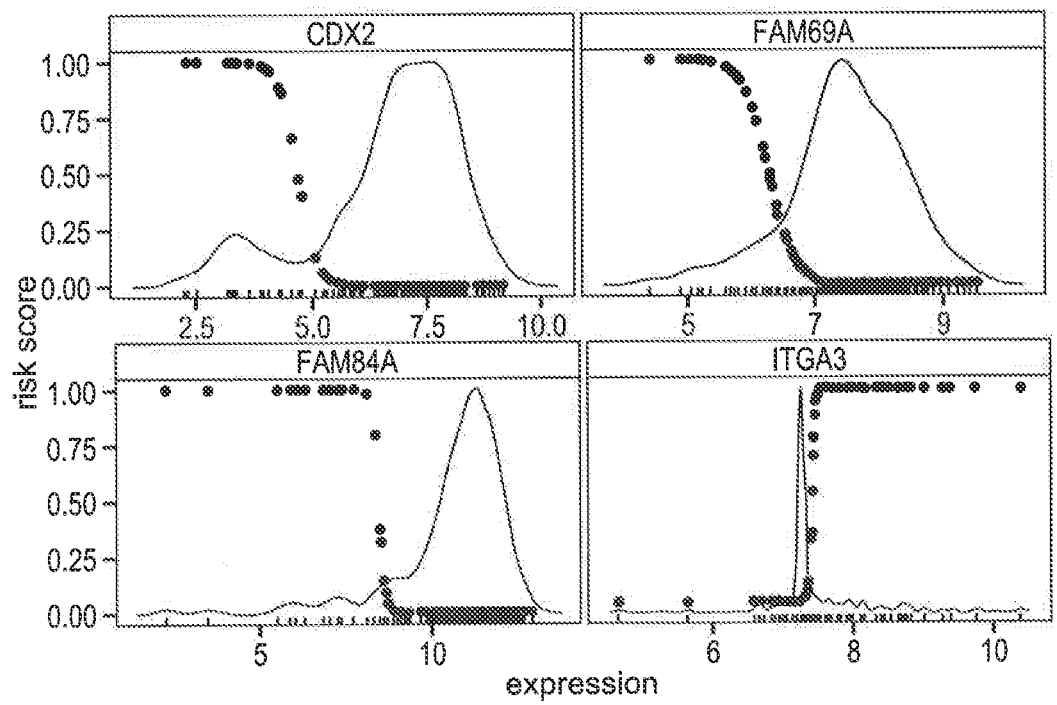

FIG. 1 illustrates the relevant features of the genes that will eventually be selected for the apCL and apCR scores. Each panel is a plot of the individual gene risk scores versus the gene expression values. The density distribution of the gene's expression values, scaled to a range of 0 to 1, is superimposed on the plot. The multiple states of the genes are apparent from the density distributions and the rug plots.

Selection of the Specific Panel Genes for apCL and apCR and Definition of the Prognostic Scores The apCL score is formed by taking the sum of the risk scores for those candidate genes selected for the final panel. Begin by computing the significance of each gene's risk score in a CPH in the discovery set. The most significant gene, IBSP, is the first gene to be selected for the panel. Next two-gene scores are computed by adding the risk score for IBSP and the risk scores for the other candidate genes. The most significant pair of genes, IBSP and WNT5A and them selected as two panel genes. This process is continued until adding more genes does not produce a more significant CPH, Following this procedure, apCL is defined as the sum of risk scores for the genes, IBSP, WNT5A, NOX4, and MMP3. Repeating this process for RCC, apCR is defined as the sum of the binary variables representing FAM69A, CDX2, FAM84A and ITGA3. The panel scores are scaled to the range of 0 to 100 as described above.

Figure 2B:
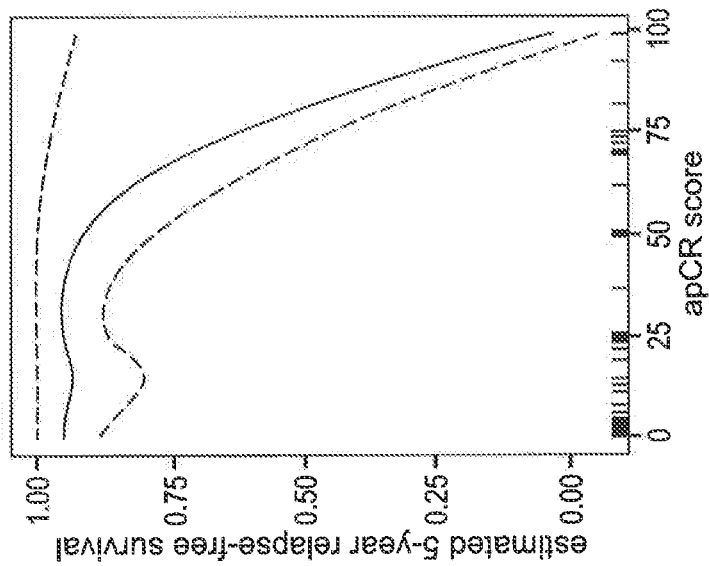
FIG. 2—The 5-year relapse-free survival probability is estimated in the microarray validation set for each value of the (a) apCL score and (b) apCR score. (a) To generate the curve, the Cox spline method (Gray, R. J. (1992). Flexible methods for analyzing survival data using splines, with applications to breast cancer prognosis. *Journal of the American Statistical Association,* 87(420), 942-951.) was applied to a Cox proportional hazard model with the continuous apCL score as the explanatory variable (p=1.76× $10^{-5}$). (b) The same method was applied to a Cox proportional hazard model with the apCR score as the explanatory variable (p=2.43×$10^{-5}$). The dotted lines indicate the 95% confidence interval on the estimated survival curve.
Figure 2A:
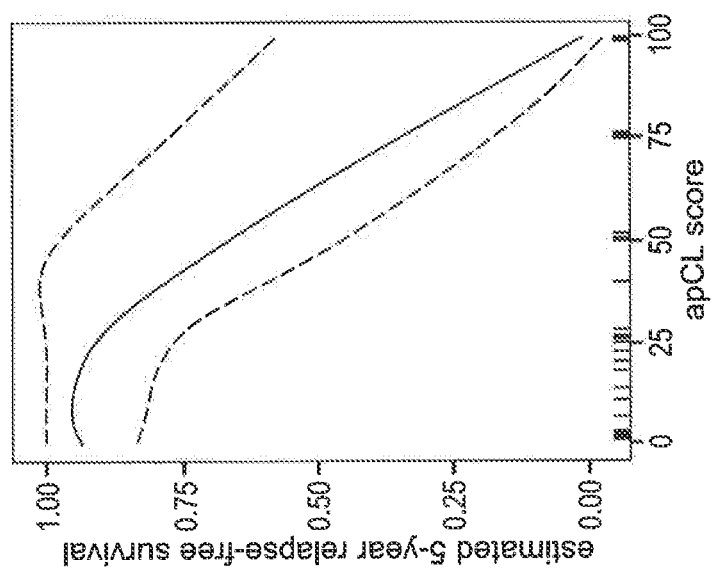

Testing the Significance of apCL and apCR in the Validation Set:

The risk scores for the apCL and apCR panel genes are extended to the LCC and RCC validation sets as described in Example 3. FIG. 2 plots the probability of relapse-free survival after 5 years versus the apCL score and apCR score. As the plot shows, the risk of relapse increases steadily with the value of the score.

Risk Stratification System with 3 Groups: Clinical application of this prognostic test will be most effective if the patients are divided into several discrete risk strata defined by intervals of apCL and apCR (Example 3). Here, the most clinically useful partition (for apCL) defines three groups Low risk, apCL 0 to less than 25;
Moderate risk, apCL greater than 25 but less than 50;
High risk, apCL of 50 to 100.

The risk strata for apCR are defined similarly. FIG. 3 plots the Kaplan-Meier survival curves for these discrete risk groups. The expected 5-year relapse-free survival probabilities for these groups are reported in Table 5.

TABLE 5

Expected survival probabilities for the discrete risk strata in the microarray validation sets

|  | apCL 5-year relapse-free survival probability (95% confidence interval) | apCR 5-year relapse-free survival probability (95% confidence interval) |
| --- | --- | --- |
| Low risk | 0.92 (0.82-1) | 0.89 (0.80-1) |
| Moderate risk | 0.74 (0.53-1) | 0.58 (0.25-1) |
| High risk | 0.34 (0.16-0.70) | 0.42 (0.19-0.93) |

Clinical applications of these risk scores will vary in stage II and stage III colon cancer because of differences in the default recommended treatment. In stage II colon cancer, chemotherapy is not recommended because it does not offer enough of an improvement in survival. In stage III colon cancer chemotherapy is recommended as the default treatment. The present test/method/stratification system can be used to identify high risk stage II patients who may benefit for administering chemotherapy and low risk stage III patients who are very unlikely to benefit from chemotherapy. For these reasons, it is important to assess the significance of apCL and apCR in separate disease stages. In the microarray data, Dukes' stage is reported, so this is used as a surrogate for today's more common staging. FIG. 4 plots the expected survival for the apCL risk strata in Dukes' B and Dukes' C LCC in the microarray data; FIG. 5 reports the corresponding results in RCC.

Advantages of the current scoring methodology for LCC and/or RCC disease compared to a binary classification in prognostic significance The prognostic test reported in a previous methodology employed by the present inventors defines a good prognosis group and a poor prognosis group using the binary multistate gene method summarized in Example 3 using the same microarray dataset. In LCC, all good prognosis samples under the binary classification are low risk with the apCL stratification. However, the poor prognosis samples defined by the binary test is further stratified by the apCL stratification identifies a small low risk group, none of which relapse, 44% of samples are moderate risk with 5-year relapse-free survival probability 0.74 (95% CI 0.53-1) and 44% high risk samples with 5-year relapse-free survival probability 0.34 (95% CI 0.16-0.70). The 5-year expected survival probability for the entire poor prognosis samples defined by the binary test is 0.57 (95% CI 0.42-0.78). Given this prognosis estimate, a physician would recommend chemotherapy for anyone in the poor prognosis group. However, chemotherapy is not recommended for a group of patients with expected survival above 0.67, namely, for the low and moderate risk patients in this group. Use of this test will reduce overtreatment in LCC by 56%.

In RCC, the binary poor risk group is also significantly stratified by the apCR test, although with potentially different clinical results. The moderate risk group here has expected survival 0.58 (0.25-1) and the high risk group has expected survival 0.42 (0.19-0.93). Thus, with apCR chemotherapy will be recommended for almost all patients in the binary poor prognosis group, however the high risk patients may be recommended for more aggressive treatment than the moderate risk patients.

Example 5

Identification of RT-PCR Probes for Measurement of Candidate Gene Expression in FFPE Tissue The process used to extract mRNA from an FFPE tissue source is described in the Methods section herein. RT-PCR primer probes were identified for all 18 candidate genes listed in Table 3 and Table 4 and the control gene, YWHAZ (Table 6). The sequences identified in Table 6 are unique, and do not reflect the sequencing of any previously naturally occurring nucleic acid sequence. They, therefore, constitute specific novel embodiments of the present invention as a set of probes as defined in Table 6 below.

TABLE 6

RT-PCR primer sequences (5'-3')

| Gene | Forward | SEQ ID NO: | Reverse | SEQ ID NO: | Threshold |
|---|---|---|---|---|---|
| ANKRD6 | ACTGCTTTCTGTTCTGTCCA | 1 | TGTGATTTAGGGCAGCAG | 20 | 0.60 |
| CDX2 | GAACCTGTGCGAGTGGATG | 2 | TCCTCCGGATGGTGATGTAG | 21 | 0.10 |
| CYP1B1 | TGGAGTTTACCTGGCTTATT | 3 | CAGCCTCCAAATTCAGTTA | 22 | 0.10 |
| FAM69A | AGACTACCTACTGCGTGGTG | 4 | ATTTCCATTTGATTTGCTGT | 23 | 0.10 |
| FAM84A | CTTCCTCTCCTCCTGATCTC | 5 | CAGGAAGAACTGAACTGTGG | 24 | 0.10 |
| IBSP | GACAGTTCAGAAGAGGAGGAG | 6 | TCTCAGCCTCAGAGTCTTCA | 25 | 0.20 |
| ITGA3 | TATTGAGGACATGTGGCTTG | 7 | ACAGCACCTGGGTGTAGC | 26 | 0.08 |
| ITPRIP | TGTGAGACGCATGTTGAAGG | 8 | GTCACCACCACCAGACACAC | 27 | 0.10 |
| MATN3 | CAGCTCTTGATAGGTGTGCT | 9 | CACAATGATAAGAGCCACTTC | 28 | 0.10 |
| MMP3 | CCAGGGATTAATGGAGATG | 10 | CAATTTCATGAGCAGCAAC | 29 | 0.08 |
| MMP28 | TCCTTTCAAGAGGTAACAGC | 11 | TCGAATTTCTCTGCTGAGTT | 30 | 0.10 |
| NOX4 | GCCATGAAGCAGGACTCTAAAGA | 12 | TTGGCATAACACAGCTGATTGAT | 31 | 0.10 |
| PCSK5 | GACCCACAGTTTCATTTCAA | 13 | GGCACGACTGAAGTCATAAT | 32 | 0.10 |
| RAB3B | CTGGGCTACTCAGATCAAGA | 14 | TCTCTTCCTCCATGTCACAC | 33 | 0.08 |
| SCL16A6 | GAGAATGTTTCGCTGTGTTT | 15 | AAGAGGAGGCTGTATCTCCA | 34 | 0.20 |
| SMAD3 | GTCAACACCAAGTGCATCA | 16 | CGGCAGTAGATGACATGAG | 35 | 0.20 |
| TFAP2C | GACATGCCTCACCAGATG | 17 | CGAATGACTGTCTGATCGTG | 36 | 0.08 |
| WNT5A | CTCGCCATGAAGAAGTCC | 18 | GAACTTGGAAGACATTGCAC | 37 | 0.30 |
| YWHAZ | ACTTTTGGTACATTGTGGCTTCAA | 19 | CCGCCAGGACAAACCAGTAT | 38 | 1.00 |

Measurement of gene expression from an FFPE tissue source is challenging because the preservation process fragments the mRNA. The probes in this table are all customized to identify short mRNA sequences that uniquely represent the particular gene.

Translation of a Genomic Test from Fresh Frozen Tissue to an FFPE Tissue Source

The translation of a genomic test from fresh-frozen tissue to an FFPE tissue source requires that measurement of the corresponding mRNA species from both tissue sources are comparable. To test that the RT-PCR primer probes for the present candidate genes produce comparable measurements in the two forms of the tissue, RT-PCR was performed on mRNA extracted from fresh and FFPE sources prepared from two colon cancer cell lines, namely DLD-1 and HCT 116. These two cell lines were chosen because DLD-1 reportedly originates from a left-side colon cancer sample [14], and the present data supports that HCT 116 originates from a right-side sample[7, 15].

Figure 6A:
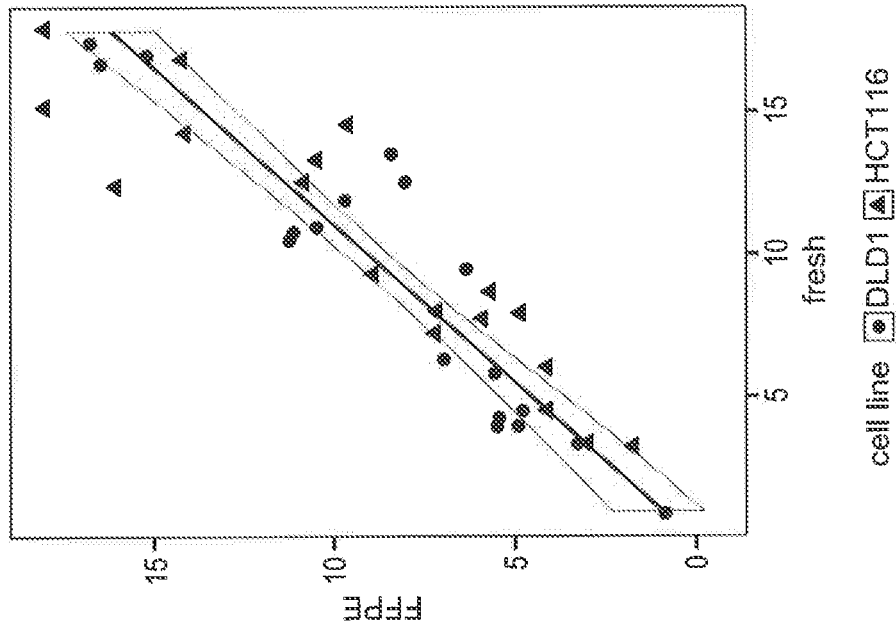
FIG. 6 Comparison of ΔCT values obtained from fresh and FFPE-preserved cell lines. (a) ΔCT values for each of the candidate genes were obtained from fresh and FFPE samples of two cell lines. (b) A line is fit to the ΔCT values obtained from fresh versus FFPE tissue for each of the candidate genes. The region defined by one standard error is shaded in gray.
Figure 6B:
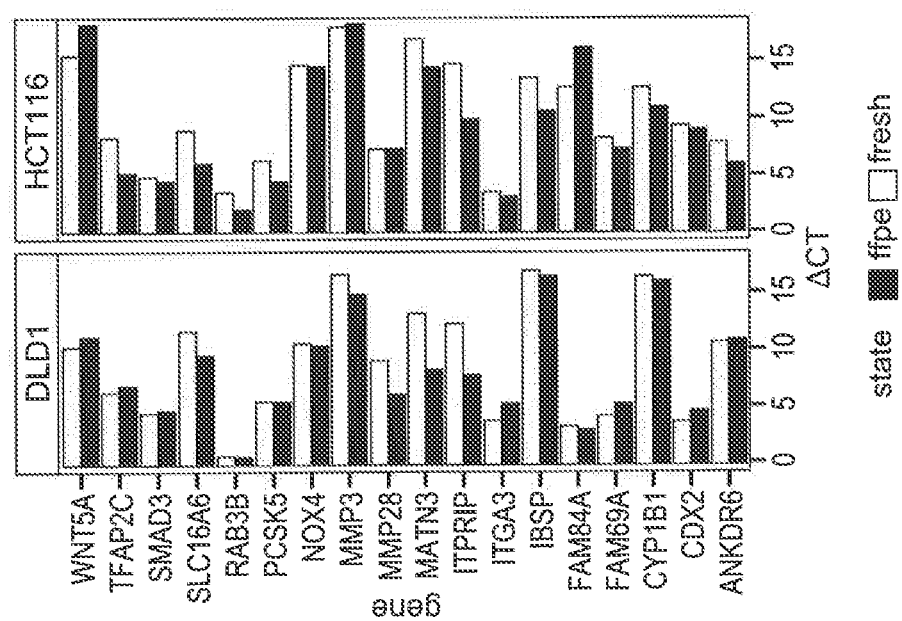

Expression levels (ΔCT) for the 18 candidate genes for fresh and FFPE samples from the two cell lines are displayed in FIG. 6a. In FIG. 6b, 36 data points were selected, one for each gene and both cell lines, with fresh expression level as the x coordinate and FFPE expression level as the y coordinate. Ideally, a line fitted to these points will have slope 1. In reality, the line has slope 0.92 (s.e. 0.069). Thus, ranging over all of these genes, measurements of candidate gene expression levels of the LCC disease associated gene targets and the RCC disease associated gene targets are comparable between fresh and FFPE tissue sources.

Example 6

Stratification of Relapse Risk by apCL and apCR Using FFPE Tissue

Using a validation set of FFPE colon cancer tissue with a record of relapse events for at least 5 years, the apCL and apCR tests are translated to the present methodology and to asses performance therein.

Selection of the Independent FFPE Validation Sample Set

Preliminary validation of apCR and apCL is combined with translation to an FFPE tissue source and expression measurement with RT-PCR using a novel set of FFPE colon cancer samples. The characteristics of the samples are described in the Methods section and Table 2. Most importantly, all samples are from patients with stage II colon cancer and none received adjuvant chemotherapy. The survival endpoint is any relapse, including local relapse, distant metastasis or death due to colon cancer.

Calculation of individual gene risk scores from RT-PCR measurements, and the associated apCL and apCR.

The process of using mixture model methodology to calculate individual gene risk scores is identical to that used in the microarray data. The apCL and apCR scores are then the sums of the panel gene risk scores scaled to the range 0 to 100.

Performance of apCL and apCR in the FFPE Sample Set

The 5-year relapse-free survival probabilities for the apCR and apCL risk groups in the FFPE sample set are reported in Table 7. There is an insufficient number of samples to reach statistical significance, however the trends in the risk groups match those validated previously in the microarray dataset.

TABLE 7

Relapse-free survival properties of the apCL and apCR risk groups in the FFPE samples

|  | apCL 5-year relapse-free survival probability (95% confidence interval) | apCR 5-year relapse-free survival probability (95% confidence interval) |
| --- | --- | --- |
| Low risk | 0.92 (0.82-1) | 0.89 (0.801) |
| Moderate risk | 0.74 (0.53-1) | 0.58 (0.25-1) |
| High risk | 0.34 (0.16-0.70) | 0.42 (0.19-0.93) |

Stratification of Relapse Risk by the FFPE Versions of apCL and apCR

The binary variables defined with the left-side genes for the FFPE samples are added to form FFPE version of the apCL score, denoted f-apCL. The right-side score, f-apCR, is defined correspondingly. The strata defined by scores greater than 1 are merged into one strata in these samples, because they are individually too small to yield meaningful results. The Kaplan-Meier survival plots for f-apCL and f-apCL to ether with tables of the numbers of samples at risk, are shown in FIG. 5. Most importantly, the 5-year expected survival probabilities for the poorest prognosis strata are very low.

Example 7

Use of Stratification Data in Colon Cancer Treatment Strategies

The present example is provided to demonstrate the utility of the present invention for developing personalized treatment regimens for a patient having colon cancer. There are many different forms of chemotherapy, some being more patient-adverse and aggressive than others. Almost all adjuvant chemotherapies have many associated adverse side-effects, and contribute to the deterioration of a patient's quality of life during therapy. For example, nausea, hair loss, short-term memory loss, loss of energy/low energy, lethargy, weight loss, etc, are just a few of the side-effects of these treatments. Moreover, chemotherapy is a significant financial burden on the healthcare system, which is wasted when it has no significant benefit to the patient's long-term survival or quality of life.

With the present protocol, a colon cancer patient may be exposed to a chemotherapy treatment regimen that is commensurate with the individual patient's risk of relapse free survival without chemotherapy, or a colon cancer patient will be classified into one of four groups based on the patient's score as determined according to the present invention.

For a group of patients, chemotherapy isn't recommended unless there is a measurable reduction in the risk of relapse following treatment. Doctors would normally not administer chemotherapy if the reduction in the overall risk of relapse is ≤4%. Conversely, if the reduction in risk of relapse is 6%, treatment with chemotherapy may be recommended. These thresholds may vary depending on other factors, such as the age of the patient, the patients overall health, the patients preference for less/more aggressive chemotherapeutic or other treatment approaches, other types of treatment intervention available, etc.

Standard chemotherapy for colon cancer results in an 18% reduction in relapses. Moreover, this percentage is the same in stage II and stage III disease. Thus, in collection of colon cancer samples in with the over relapse rate is x, the overall reduction in relapse due to chemotherapy is (0.18)(x). The thresholds of 4% and 6% indicated above translate to the following thresholds for x and interpretations for treatment:

Chemotherapy is not recommended for a group if the overall risk of survival is less than or equal to x=(0.04)/(0.18)=0.22; that is the relapse-free survival probability is ≥0.88;

Chemotherapy is recommended for a group if the overall risk of survival is greater than or equal to x=(0.06)/(0.18)=0.33; that is, the relapse-free survival probability is ≤0.67;

A group with expected survival between 0.88 and 0.67 would be unlikely to have a definite recommendation for treatment. Treatment could be decided based on other risk factors such as age and general health.

In the microarray LCC validation set, the expected survival probabilities for the Low, Moderate and High risk groups defined by apCL are 0.92, 0.74 and 0.34, respectively. Thus, chemotherapy would be recommended for the High risk group, not recommended for the Low risk group, and indeterminate for the Moderate risk group.

For RCC, the apCR Low, Moderate and High risk groups have survival probabilities 0.89, 0.58 and 0.42, respectively. In this case, the High risk group would be recommended for chemotherapy. However, the High risk group has significantly poorer prognosis than the Moderate risk group. If it is available, more aggressive treatment is justified. For the Moderate risk group, a further step may include further clinical testing to identify additional potential risk factors and/or sensitivity to specific forms of chemotherapy. This further testing would, for example, include examining the sample for the presence of specific families of mutations that have been identified as affecting the patient's risk of relapse and/or the patient's potential responsiveness to specific forms of chemotherapy (CAP's Technology Assessment Committee, Prognostic Uses of MSI Testing, College of American Pathologists, 2011). These mutations include, for example, microsatellite instability (i.e., mutations in mismatch repair genes), mutation of BRAF and mutation of KRAS. While none of these particular tests, singly or in combination, can match the prognostic power of the presently described ap family of tests as described here, they may be recommended as further screening/testing options for the patient categorized in the moderate risk stratum, having a apCL and/or apCR score of from 25 to 50. In this manner, a patient in the moderate risk group may yield a test result in a subsequent genetic testing screen that provides a recommendation for a specific chemotherapy treatment.

Several drugs and drug combinations are used as chemotherapy treatment for colon cancer. (Hagop M. Kantarjian, Robert A. Wolff, Charles A. Koller, The MD Anderson Manual of Medical Oncology, Second Edition, McGraw-Hill (2011).

The four common drugs are

5-Fluorouracil (5-FU) which is often given with leucovorin (folic acid), which improves its effectiveness;

Capecitabine, which is transformed into 5-FU when it reaches the tumor site;

Irinotecan;

Oxaliplatin

Irinotecan

The first two drugs are moderately effective. Oxaliplatin is the most effective, but has greater side-effects. Oxaliplatin also has been reported to not penetrate tumors, it only treats cells on the outer layer of tumors and is considered relatively worthless for treatment of cells within the core of a tumor. The most high risk patients may be treated with FOLFOX, a combination of 5-FU, leucovorin and Oxaliplatin.

These options for different chemotherapy regimes with increasing levels of effectiveness, offset by increasingly serious side effects, call for flexible risk assessments. A patient with expected survival 0.65 may be given the mildest form of chemotherapy, namely 5-FU, while a patient with expected survival 0.34 may be recommended for Oxaliplatin. As new drugs become available, the recommendations may change, underscoring the usefulness of a continuous risk assessment. The risk groups defined as follows using apCL and apCR would have direct clinical application The four groups as used in the assessment of relapse risk for Right Side Colon Cancer (RCC) patient is as follows:
1. Good—Risk of Relapse score of 0 to less than 25. Risk of relapse for RCC patient without post-surgical adjuvant chemotherapy is very low.
2. Fair—Risk of Relapse score of 25 to less than 50. Risk of relapse for RCC patient without post-surgical adjuvant chemotherapy is moderate.
3. Poor—Risk of Relapse score of 50 to less than 75. Risk of Relapse for RCC patient without post-surgical adjuvant chemotherapy is high.
4. Very Poor—Relapse-free score of 75 to 100. Risk of relapse for RCC patient without post-surgical adjuvant chemotherapy is very high.

The four groups as used in the assessment of relapse risk for Left Side Colon Cancer (LCC) patient is as follows:
1. Good—Risk of Relapse score of 0 to less than 25. Risk of relapse for LCC patient without post-surgical adjuvant chemotherapy is very low.
2. Fair—Risk of Relapse score of 25 to less than 50. Risk of relapse for LCC patient without post-surgical adjuvant chemotherapy is low.
3. Poor—Risk of Relapse score of 50 to less than 75. Risk of relapse for LCC patient without post-surgical adjuvant chemotherapy is high.
4. Very Poor—Risk of Relapse score is 75 to 100. Risk of Relapse for LCC patient without post-surgical adjuvant chemotherapy is very high.

Based on the risk of relapse group into which the individual patient's score places them (good, fair, poor, very poor), the attending clinician may prescribe an appropriate treatment modality and level of treatment for the patient that is more closely tailored to the patients individually assessed risk of relapse. For example, a more aggressive chemotherapy or other aggressive anti-cancer treatment regimen may be paired with a patient having been assessed to have a "Very Poor" 5-year relapse free survival score in the absence of chemotherapy. In the event that a colon cancer patient is assessed as having a "Good" 5-year relapse-free survival outcome in the absence of chemotherapy, then the clinician may avoid more aggressive adjuvant chemotherapy regimens, and instead present the option of receiving no further chemotherapy post-surgery, or a milder form of chemotherapy regimen.

Impact on Reduction in Colon Cancer Lethality from Chemotherapy Under-treatment and Lost Quality of Life Due to Chemotherapy Over-treatment Currently, stage II colon cancer patients are not recommended for chemotherapy. The 5-year relapse-free survival probability for stage II colon cancer is approximately 0.80. Of the 100,000 new colon cancer cases each year in the U.S., about half of them are stage II. Of these 50,000 patients, 10,000 are likely to succumb to the disease. With the introduction of apCL and apCR, the patients assessed as High risk will be recommended for chemotherapy, while the Low and Moderate risk patients may be excused from chemotherapy. The expected survival in the Low and Moderate risk groups, which is about 75% of the cases, is 0.90. In other words, only about 3,750 of the expected deaths will be from the Low and Moderate risk groups. The remaining 6,250 deaths occur in the 12,500 cases in the High risk group. The recommended chemotherapy treatment of these patients will reduce the mortality by 18%. That is a reduction of (0.18) (6250)=1125 deaths. In conclusion, treating with standard chemotherapy the 12,500 High risk stage II colon cancer patients identified by our test is likely to save 1,125 patients from death due to colon cancer.

There are about 25,000 new stage III colon cancer patients in the U.S. each year. All of these are currently recommended for chemotherapy. Half of these patients are classified as Low risk by our test. Since chemotherapy will have a marginal benefit for these patients, treatment will not be recommended for them. Thus, 12,500 patients will be excused from chemotherapy with no measurable change in the treatment affect of chemotherapy on overall deaths due to colon cancer.

Example 8

Computer and Electronic Reporting and Assessment Systems of RCC and LCC Disease Assessment and Reporting The present example is provided to demonstrate the utility of the present invention for providing assessment and prognostic tools that may be electronically utilized by a health care professional, professional diagnostic lab, health care organization, hospital data reporting system or other medical data provider system.

In some embodiments, the present invention provides computer programming for analyzing and comparing a first and a second pattern of the LCC and/or RCC disease specific marker detection results from a sample taken at least two different time points. In other embodiments, the first pattern may be indicative of a pre-cancerous condition and/or low relapse risk LCC and/or RCC condition and/or progression from a low relapse risk LCC and/or RCC condition to a higher relapse risk LCC and/or RCC condition. In such embodiments, the comparing provides for monitoring of the progression of the LCC and/or RCC condition from the first time point to the second time point.

In yet another embodiment, the invention provides computer programming for analyzing and comparing a pattern of LCC and/or RCC-specific marker detection and/or measurement results from a sample to a library of LCC and/or RCC disease-specific marker patterns known to be indicative of the presence or absence of a the LCC and/or RCC disease, wherein the comparing provides, for example, a differential diagnosis between a low RCC and/or LCC relapse risk, and a high RCC and/or LCC relapse risk condition (e.g., the RCC and/or LCC gene panel marker levels, scores and patterns providing for staging and/or grading of the LCC and/or RCC disease condition).

The methods and systems described herein can be implemented in numerous ways. In one embodiment, the methods involve use of a communications infrastructure, for example the internet. It is also to be understood that the present invention may be implemented in various forms of hardware, software, firmware, processors, distributed servers (e.g., as used in cloud computing) or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site (e.g., at a service provider's facility).

For example, during or after data input by the user, portions of the data processing can be performed in the user-side computing environment. For example, the user-side computing environment can be programmed to provide for defined test codes to denote platform, carrier/diagnostic test, or both; processing of data using defined flags, and/or generation of flag configurations, where the responses are transmitted as processed or partially processed responses to the reviewer's computing environment in the form of test code and flag configurations for subsequent execution of one or more algorithms to provide a results and/or generate a report in the reviewer's computing environment.

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which generally includes test data (e.g., specific gene products assayed), and test result data (e.g., the pattern of gastrointestinal neoplasm-specific marker detection results from a sample). This information received can be stored at least temporarily in a database, and data analyzed in comparison to a library of marker patterns known to be indicative of a stage and/or grade of RCC and/or LCC disease.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include email, interactive television, and the like. In some embodiments, all or a portion of the input data and/or all or a portion of the output data (e.g., usually at least the library of the pattern of LCC and/or RCC disease detection results known to be indicative of the relative risk of relapse for the LCC and/or RCC disease) are maintained on a server for access, e.g., confidential access. The results may be accessed or sent to professionals as desired.

A system for use in the methods described herein generally includes at least one computer processor (e.g., where the method is carried out in its entirety at a single site) or at least two networked computer processors (e.g., where detected marker data for a sample obtained from a subject is to be input by a user (e.g., a technician or someone performing the assays)) and transmitted to a remote site to a second computer processor for analysis (e.g., analysis of the expression levels of the RCC and/or LCC specific gene panel in a patient specimen and classified into a "poor" to "good" risk or relapse prognosis group, relative to a reference population of RCC and/or LCC gene levels), where the first and second computer processors are connected by a network, e.g., via an intranet or internet). The system can also include a user component(s) for input; and a reviewer component(s) for review of data, and generation of reports, including classification/stratification of a LCC and/or RCC disease, or monitoring the progression of a LCC and/or RCC disease in a patient. Additional components of the system can include a server component(s); and a database(s) for storing data (e.g., as in a database of report elements, e.g., a library of marker patterns known to be indicative of the LCC and/or RCC disease panel as described herein, or absence of a LCC and/or RCC disease and/or known to be indicative of a risk of relapse stage of the LCC and/or RCC disease, or a relational database (RDB) which can include data input by the user and data output. The computer processors can be processors that are typically found in personal desktop computers (e.g., IBM, Dell, Macintosh), portable computers, mainframes, minicomputers, or other computing devices.

The input components can be complete, stand-alone personal computers offering a full range of power and features to run applications. The user component usually operates under any desired operating system and includes a communication element (e.g., a modem or other hardware for connecting to a network), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe, or distributed across multiple servers (e.g., as in cloud computing applications) and offers data management, information sharing between clients, network administration and security. The application and any databases used can be on the same or different servers. Other computing arrangements for the user and server(s), including processing on a single machine such as a mainframe, a collection of machines, or other suitable configuration are contemplated. In general, the user and server machines work together to accomplish the processing of the present invention.

Where used, the database(s) is usually connected to the database server component and can be any device which will hold data. For example, the database can be any magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc. as desired.

Example 9

Microchip for use in Colon Cancer Stratification Method for LCC and RCC

The present example demonstrates the utility of the invention for providing a microchip useful in the screening of patient samples, including FPPE samples, using the RCC gene panel and the LCC gene panel provided herein.

The microchip will be prepared using a solid substrate. This solid substrate, for example, may be made of synthetic materials or natural materials, optionally chemically modified, in particular polysaccharides such as cellulose-based materials, for example paper, cellulose derivatives such as cellulose acetate and nitrocellulose or dextran, polymers, copolymers, in particular based on styrene-type monomers, natural fibers such as cotton, and synthetic fibers such as nylon; inorganic materials such as silica, quartz, glasses or ceramics; latices; magnetic particles; metal derivatives, gels, etc. The solid substrate may be in the form of a microtitration plate, of a membrane as described in application WO-A-94/12670 or of a particle. It is also possible to immobilize on the substrate several different capture probes, each being specific for a target gene. In particular, a biochip on which a large number of probes can be immobilized may be used as substrate.

The term "biochip" is intended to mean a solid substrate that is small in size, to which a multitude of capture probes are attached at predetermined positions. The biochip, or DNA chip, concept dates from the beginning of the 1990s. It is based on a multidisciplinary technology that integrates microelectronics, nucleic acid chemistry, image analysis and information technology. The operating principle is based on a foundation of molecular biology: the hybridization phenomenon, i.e. the pairing, by complementarity, of the bases of two DNA and/or RNA sequences. The biochip method is based on the use of "capture probes" attached to a solid substrate, on which probes of a sample of target nucleotide fragments, directly or indirectly labeled with fluorochromes or other label, is made to act. The "capture probes" will be positioned specifically on the substrate or chip. Each hybridization gives a specific piece of information, in relation to the target nucleotide fragment. The pieces of information obtained are cumulative, and make it possible, for example, to quantify the level of expression of one or more target genes. In order to analyze the expression of a target gene, a substrate comprising a multitude of probes, which correspond to all or part of a "target gene" which is transcribed to mRNA, can then be prepared.

For the purpose of the present invention, the term "low-density substrate" is intended to mean a substrate comprising fewer than 50 probes. For the purpose of the present invention, the term "medium-density substrate" is intended to mean a substrate comprising from 50 probes to 10 000 probes. For the purpose of the present invention, the term "high-density substrate" is intended to mean a substrate comprising more than 10 000 probes.

The cRNAs or cDNAs specific for a nucleic acid of a "target gene" that it is desired to be analyze are hybridized, for example, to specific "capture probes". After hybridization, the substrate or chip is washed, and the labeled cDNA or cRNA/capture probe complexes are revealed by means of a high-affinity ligand bound, for example, to a fluorochrome-type label. The fluorescence or other label may then be read, for example, with a scanner. The analysis of the fluorescence or other marker/label may then be processed by information technology.

By way of indication, mention may be made of the DNA chips developed by the company Affymetrix ("Accessing Genetic Information with High-Density DNA arrays," M. Chee, et al., Science 1996, 274, 610-614. "Light-generated oligonucleotide arrays for rapid DNA sequence analysis," A. Caviani Pease, et al., Proc. Natl. Acad. Sci. USA, 1994, 91, 5022-5026), for molecular diagnoses. In this technology, the "capture probes" are generally small in size, around 25 nucleotides. Other examples of biochips are given in the publications by G. Ramsay, Nature Biotechnology, 1998, No. 16, p. 4044; F. Ginot, Human Mutation, 1997, No. 10, p. 1-10; J. Cheng, et al., Molecular diagnosis, 1996, No. 1 (3), p. 183-200; T. Livache, et al., Nucleic Acids Research, 1994, No. 22 (15), p. 2915-2921 J. Cheng, et al., Nature Biotechnology, 1998, No. 16, p. 541-546 or in U.S. pat. Nos. 4,981,783 5,700,637, 5,445,934, 5,744,305 and 5,807,522. The main characteristic of the solid substrate should be to conserve the hybridization characteristics of the "capture probes" on the target nucleotides fragments while at the same time generating a minimum background noise for the method of detection.

The probes may be immobilized onto the solid substrate by several techniques. For example, one technique consists of depositing pre-synthesized probes. The attachment of the probes may be carried out by direct transfer, by means of micropipettes, microdots or by means of an inkjet device. This technique allows the attachment of probes having a size ranging from a few bases (5 to 10) up to relatively large sizes of 60 bases (printing) to a few hundred bases (microdeposition). Printing is an adaptation of the method used by inkjet printers. It is based on the propulsion of very small spheres of fluid (volume<1 nl) at a rate that may reach 4000 drops/second. Printing does not involve any contact between the system releasing the fluid and the surface on which it is deposited. Microdeposition consists in attaching long probes of a few tens to several hundred bases to the surface of a glass slide. These probes are generally extracted from databases and are in the form of amplified and purified products. This technique makes it possible to produce chips called microarrays that carry approximately ten thousand spots, called recognition zones, of DNA on a surface area of a little less than 4 cm$^{(2)}$. The use of nylon membranes, referred to as "macroarrays", which carry products that have been amplified, generally by PCR, with a diameter of 0.5 to 1 mm and the maximum density of which is 25 spots/cm$^2$, is another example. A certain volume of sample can, however, be deposited at the bottom of a microtitration plate, in each well, as in the case in patent applications WO-A-00/71750 and FR 00/14896, or a certain number of drops that are separate from one another can be deposited at the bottom of one and the same Petri dish, according to another patent application, FR 00/14691.

A second general technique for attaching probes to a solid substrate or chip is in situ synthesis. This technique results in the production of short probes directly at the surface of the chip. It is based on in situ oligonucleotide synthesis (see, in particular, patent applications WO 89/10977 and WO 90/03382), and is based on the oligonucleotide synthesizer process. This process consists in moving a reaction chamber, in which the oligonucleotide extension reaction takes place, along the glass surface.

A third general technique is called photolithography. This process is used in biochips developed by AFFYMETRIX. This is an in situ synthesis. Photolithography is derived from microprocessor techniques. The surface of the chip is modified by the attachment of photolabile chemical groups that can be light-activated. Once illuminated, these groups are capable of reacting with the 3' end of an oligonucleotide. By protecting this surface with masks of defined shapes, it is possible to selectively illuminate and therefore activate areas of the chip where it is desired to attach one or other of the four nucleotides. The successive use of different masks makes it possible to alternate cycles of protection/reaction and therefore to produce the oligonucleotide probes on spots of approximately a few tens of square micrometers (μm 2). This resolution makes it possible to create up to several hundred thousand spots on a surface area of a few square centimeters ($cm.^2$). All these techniques can be used with the present invention.

According to a preferred embodiment, the technique preferred includes at least one hybridization probe that is immobilized on the solid substrate. This substrate is preferably a low-, high- or medium-density substrate as defined above.

The hybridization of a multitude of probes onto a solid substrate is typically preceded by an enzymatic amplification reaction step in order to increase the amount of target genetic material. The determination of the expression level of a "target gene" (i.e., the genes identified in the LCC (4 to 9 genes) and/or RCC (4 to 9 genes) panel genes) can be carried out by any of the protocols known to those skilled in the art. In general, the expression of a "target gene" can be analyzed by detecting the mRNAs (messenger RNAs) that are transcribed from the target gene at a given moment.

The invention preferably relates to the determination of the expression level of a target gene by detection of the mRNAs derived from this target gene according to any of the protocols well known to those skilled in the art. According to a specific embodiment of the invention, the expression level of several target genes is determined simultaneously, by detection of several different mRNAs, each mRNA being derived from a target gene, such as those target genes identified in the LCC gene panel and RCC gene panel herein.

By way of amplification, it is possible, to determine the expression level of the target gene as follows: 1) After extracting the total RNA (comprising the transfer RNAs (tRNAs), the ribosomal RNAs (rRNAs) and the messenger RNAs (mRNAs)) from a tissue sample (fresh-frozen or FFPE), a reverse transcription step is carried out in order to obtain the complementary DNAs (cDNAs) of said mRNAs. This reverse transcription reaction can be carried out using a reverse transcriptase enzyme which makes it possible to obtain, from an RNA fragment, a complementary DNA (cDNA) fragment. The reverse transcriptase enzyme from AMV (Avian Myoblastosis Virus) or from MMLV (Moloney Murine Leukaemia Virus) can in particular be used.

When it is more particularly desired to obtain only the cDNAs of the mRNAs, this reverse transcription step is carried out in the presence of nucleotide fragments comprising only thymine bases (polyT), which hybridize by complementarity to the polyA sequence of the mRNAs so as to form a polyT-polyA complex, that then serves as a starting point for the reverse transcription reaction carried out by the reverse transcriptase enzyme.

cDNAs complementary to the mRNAs derived from a target gene (target-gene-specific cDNA) and cDNAs complementary to the mRNAs derived from genes other than the target gene (cDNAs not specific for the target gene) are then obtained. The amplification primer(s) specific for a target gene is (are) then brought into contact with the target-gene-specific cDNAs and the cDNAs not specific for the target gene. The amplification primer(s) specific for a target gene will hybridize(s) with the target-gene-specific cDNAs and a predetermined region, of known length, of the cDNAs originating from the mRNAs derived from the target gene is specifically amplified. The cDNAs not specific for the target gene are not amplified, whereas a large amount of target-gene-specific cDNAs is then obtained. For the purpose of the present invention, reference is made, without distinction, to "target-gene-specific cDNAs" or to "cDNAs originating from the mRNAs derived from the target gene". This step can be carried out in particular by means of a PCR-type amplification reaction or by any other amplification technique as defined above. By PCR, it is also possible to simultaneously amplify several different cDNAs, each one being specific for a specific target gene, by using several pairs of different amplification primers, each one being specific for a target gene: reference is then made to multiplex amplification. The expression of the target gene is determined by detecting and quantifying the target-gene-specific cDNAs obtained as described above. This detection can be carried out after electrophoretic migration of the target-gene-specific cDNAs according to their size. The gel and the medium for the migration can include ethidium bromide so as to allow direct detection of the target-gene-specific cDNAs when the gel is placed, after a given migration period, on a UV (ultraviolet)-ray light table, through the emission of a light signal. The greater the amount of target-gene-specific cDNAs, the brighter this light signal. These electrophoresis techniques are well known to those skilled in the art. The target-gene-specific cDNAs can also be detected and quantified using a quantification range obtained by means of an amplification reaction carried out until saturation.

In order to take into account the variability in enzymatic efficiency that may be observed during the various steps (reverse transcription, PCR, etc.), the expression of a target gene of various groups of patients can be normalized by simultaneously determining the expression of a "housekeeping" gene, the expression of which is similar in the various groups of patients. By way of example, the particular "housekeeping gene" to be employed in some embodiments of the present invention is the YWHAZ. By realizing a ratio of the expression of the target gene to the expression of the housekeeping gene, i.e. by realizing a ratio of the amount of target-gene-specific cDNAs to the amount of housekeeping-gene-specific cDNAs, any variability between the various measurements is thus corrected. Those skilled in the art may refer in particular to the following publications: Bustin S A, J Mol Endocrinol, 2002, 29: 23-39; Giulietti A Methods, 2001, 25: 386-401.

For hybridization, the expression of a target gene can be determined as follows. After having extracted the total RNA from the patient sample (i.e., an FFPE sample, or fresh-frozen tissue sample), a reverse transcription step is carried out as described above in order to obtain cDNAs complementary to the mRNAs derived from a target gene (target-gene-specific cDNA) and cDNAs complementary to the mRNAs derived from genes other than the target gene (cDNA not specific for the target gene). All the cDNAs are brought into contact with a substrate, on which are immobilized "capture probes" specific for the target gene whose expression it is desired to analyze, in order to carry out a hybridization reaction between the target-gene-specific cDNAs and the capture probes. (See Table 3 (LCC gene panel probes) and Table 4 (RCC gene panel probes)). The cDNAs not specific for the target gene not hybridizing to the capture probes. The hybridization reaction can be carried out on a solid substrate which includes all the materials as indicated above.

According to one embodiment, the hybridization probe(s) is/are immobilized on a solid substrate. Preferably, the substrate is a low-, high- or medium-density substrate as defined above. The hybridization reaction may be preceded by a step consisting of enzymatic amplification of the target-gene-specific cDNAs as described above, so as to obtain a large amount of target-gene-specific cDNAs, and thereby increase the probability of a target-gene-specific cDNA hybridizing to a capture probe specific for the target gene. The hybridization reaction may also be preceded by a step consisting in labeling and/or cleaving the target-gene-specific cDNAs as described above, for example using a labeled deoxyribonucleotide triphosphate for the amplification reaction. The cleavage can be carried out in particular by the action of imidazole and manganese chloride. The target-gene-specific cDNA can also be labeled after the amplification step, for example by hybridizing a labeled probe according to the sandwich hybridization technique described in document WO-A-91/19812.

Other specific methods for labeling and/or cleaving nucleic acids are described in applications WO 99/65926, WO 01/44507, WO 01/44506, WO 02/090584, WO 02/090319.3). A step consisting of detection of the hybridization reaction is subsequently carried out. The detection can be carried out by bringing the substrate on which the capture probes specific for the target gene are hybridized with the target-gene-specific cDNAs into contact with a "detection" probe labeled with a label, and detecting the signal emitted by the label. When the target-gene-specific cDNA has been labeled beforehand with a label, the signal emitted by the label is detected directly.

The expression of a target gene can also be determined using an alternative technique. For example, after having extracted the total RNA from the patient sample (FFPE tissue sample or fresh frozen tissue sample), a reverse transcription step is carried out as described above in order to obtain the cDNAs of the mRNAs of the biological material. The polymerization of the complementary RNA (cRNA) of the cDNA is subsequently carried out using a T7 polymerase enzyme which functions under the control of a promoter and which makes it possible to obtain, from a DNA template, the complementary RNA (cRNA). The cRNAs of the cDNAs of the mRNAs specific for the target gene (reference is then made to target-gene-specific cRNA), and the cRNAs of the cDNAs of the mRNAs not specific for the target gene are then obtained. All the cRNAs are brought into contact with a substrate, on which are immobilized capture probes specific for the target gene(s) whose expression it is desired to analyze, in order to carry out a hybridization reaction between the target-gene-specific cRNAs and the capture probes, the cRNAs not specific for the target gene not hybridizing to the capture probes.

When it is desired to simultaneously analyze the expression of several target genes, several different capture probes can be immobilized on the substrate, each one being specific for a target gene. The hybridization reaction may also be preceded by a step of labeling and/or cleaving the target-gene-specific cRNAs. A step of detecting the hybridization reaction is subsequently carried out. The detection can be carried out by bringing the substrate on which the capture probes specific for the target gene are hybridized with the target-gene-specific cRNA into contact with a "detection" probe labeled with a label, and detecting the signal emitted by the label. When the target-gene-specific cRNA has been labeled beforehand with a label, the signal emitted by the label is detected directly. The use of cRNA is particularly advantageous when a substrate that includes a large number of probes hybridized thereto is used. apCL and apCR Patient Data Analysis generated with the Four-Strata Stratification System Example 10

The present example presents the individual calculations obtained with patient data derived by calculations and analysis using the present methods with genetic material (cRNA, cRNA) prepared from patient samples derived right side or left side tumor tissue total RNA

| apCR - Four (4) Stratification System Patient Data Analysis | | | | | |
|---|---|---|---|---|---|
| apCR score | Survival probability | Upper 95% confidence interval | Lower 95% confidence interval | Prognosis group | Prognosis group 2 |
| 0 | 0.9138288 | 1 | 0.77958782 | good | good |
| 1 | 0.94392065 | 1 | 0.8674223 | good | good |
| 2 | 0.95813005 | 1 | 0.90661181 | good | good |
| 3 | 0.95782259 | 1 | 0.90674159 | good | good |
| 4 | 0.95300132 | 1 | 0.89252156 | good | good |
| 5 | 0.9482114 | 1 | 0.87513335 | good | good |
| 6 | 0.94382387 | 1 | 0.85694704 | good | good |
| 7 | 0.93995212 | 1 | 0.83947865 | good | good |
| 8 | 0.93668233 | 1 | 0.82382046 | good | good |
| 9 | 0.9340705 | 1 | 0.81069724 | good | good |
| 10 | 0.93214196 | 1 | 0.80053043 | good | good |
| 11 | 0.93089305 | 1 | 0.79349428 | good | good |
| 12 | 0.93029451 | 1 | 0.78956574 | good | good |
| 13 | 0.93029597 | 1 | 0.78856891 | good | good |
| 14 | 0.93083103 | 1 | 0.79021464 | good | good |
| 15 | 0.93182242 | 1 | 0.79413529 | good | good |
| 16 | 0.93318693 | 1 | 0.79991491 | good | good |
| 17 | 0.93483967 | 1 | 0.8071153 | good | good |
| 18 | 0.93669764 | 1 | 0.81529808 | good | good |
| 19 | 0.93868236 | 1 | 0.824043 | good | good |
| 20 | 0.94072175 | 1 | 0.83296248 | good | good |
| 21 | 0.9427511 | 1 | 0.84171247 | good | good |
| 22 | 0.94471339 | 1 | 0.84999991 | good | good |
| 23 | 0.94655897 | 1 | 0.85758689 | good | good |
| 24 | 0.94824476 | 1 | 0.86429177 | good | good |
| 25 | 0.94973309 | 1 | 0.86998711 | moderate | moderate |
| 26 | 0.9509941 | 1 | 0.87460745 | moderate | moderate |
| 27 | 0.95203112 | 1 | 0.87822316 | moderate | moderate |
| 28 | 0.95286057 | 1 | 0.88094928 | moderate | moderate |
| 29 | 0.95349606 | 1 | 0.8828864 | moderate | moderate |
| 30 | 0.95394867 | 1 | 0.8841212 | moderate | moderate |
| 31 | 0.95422722 | 1 | 0.8847273 | moderate | moderate |
| 32 | 0.95433845 | 1 | 0.88476624 | moderate | moderate |
| 33 | 0.95428727 | 1 | 0.88428852 | moderate | moderate |
| 34 | 0.9540769 | 1 | 0.88333473 | moderate | moderate |
| 35 | 0.95370896 | 1 | 0.88193666 | moderate | moderate | apCR - Four (4) Stratification System Patient Data Analysis

| apCR score | Survival probability | Upper 95% confidence interval | Lower 95% confidence interval | Prognosis group | Prognosis group 2 |
|---|---|---|---|---|---|
| 36 | 0.95318357 | 1 | 0.88011837 | moderate | moderate |
| 37 | 0.95249945 | 1 | 0.87789723 | moderate | moderate |
| 38 | 0.95165394 | 1 | 0.8752848 | moderate | moderate |
| 39 | 0.95064303 | 1 | 0.87228768 | moderate | moderate |
| 40 | 0.94946138 | 1 | 0.86890815 | moderate | moderate |
| 41 | 0.94810233 | 1 | 0.86514486 | moderate | moderate |
| 42 | 0.94655788 | 1 | 0.86099324 | moderate | moderate |
| 43 | 0.94481863 | 1 | 0.85644603 | moderate | moderate |
| 44 | 0.9428738 | 1 | 0.85149357 | moderate | moderate |
| 45 | 0.94071115 | 1 | 0.84612422 | moderate | moderate |
| 46 | 0.93831694 | 1 | 0.84032456 | moderate | moderate |
| 47 | 0.93567587 | 1 | 0.83407971 | moderate | moderate |
| 48 | 0.93277102 | 1 | 0.82737355 | moderate | moderate |
| 49 | 0.92958377 | 1 | 0.82018897 | moderate | moderate |
| 50 | 0.92609375 | 1 | 0.81250808 | poor | poor |
| 51 | 0.92227875 | 1 | 0.80431246 | poor | poor |
| 52 | 0.91811472 | 1 | 0.79558341 | poor | poor |
| 53 | 0.91357563 | 1 | 0.78630215 | poor | poor |
| 54 | 0.9086335 | 1 | 0.77645015 | poor | poor |
| 55 | 0.90325835 | 1 | 0.76600933 | poor | poor |
| 56 | 0.89741818 | 1 | 0.75496238 | poor | poor |
| 57 | 0.89107902 | 1 | 0.74329306 | poor | poor |
| 58 | 0.884205 | 1 | 0.73098644 | poor | poor |
| 59 | 0.87675842 | 1 | 0.71802927 | poor | poor |
| 60 | 0.86869991 | 1 | 0.70441021 | poor | poor |
| 61 | 0.85998869 | 1 | 0.69012013 | poor | poor |
| 62 | 0.85058278 | 1 | 0.67515239 | poor | poor |
| 63 | 0.84043944 | 1 | 0.65950302 | poor | poor |
| 64 | 0.8295156 | 1 | 0.64317101 | poor | poor |
| 65 | 0.81776843 | 1 | 0.62615836 | poor | poor |
| 66 | 0.805156 | 1 | 0.6084703 | poor | poor |
| 67 | 0.79163812 | 1 | 0.5901153 | poor | poor |
| 68 | 0.77717721 | 1 | 0.57110513 | poor | poor |
| 69 | 0.76173942 | 1 | 0.55145487 | poor | poor |
| 70 | 0.74529576 | 1 | 0.53118296 | poor | poor |
| 71 | 0.72782342 | 1 | 0.51031128 | poor | poor |
| 72 | 0.70930717 | 1 | 0.48886528 | poor | poor |
| 73 | 0.68974086 | 1 | 0.4668744 | poor | poor |
| 74 | 0.6691289 | 1 | 0.44437262 | poor | poor |
| 75 | 0.64748782 | 0.99487662 | 0.42139947 | poor | very poor |
| 76 | 0.62484754 | 0.98098794 | 0.39800128 | poor | very poor |
| 77 | 0.60124291 | 0.96597285 | 0.37422691 | poor | very poor |
| 78 | 0.57670847 | 0.94992215 | 0.35012623 | poor | very poor |
| 79 | 0.55129113 | 0.93296237 | 0.32576009 | poor | very poor |
| 80 | 0.5250524 | 0.91526003 | 0.30120404 | poor | very poor |
| 81 | 0.49806955 | 0.8970231 | 0.27655171 | poor | very poor |
| 82 | 0.4704365 | 0.87850124 | 0.25191826 | poor | very poor |
| 83 | 0.44226448 | 0.85998465 | 0.22744344 | poor | very poor |
| 84 | 0.41368226 | 0.84180177 | 0.20329372 | poor | very poor |
| 85 | 0.38483599 | 0.8243164 | 0.1796625 | poor | very poor |
| 86 | 0.3558884 | 0.80792497 | 0.15676772 | poor | very poor |
| 87 | 0.32701739 | 0.79305512 | 0.13484608 | poor | very poor |
| 88 | 0.29841384 | 0.78016692 | 0.11414329 | poor | very poor |
| 89 | 0.27027868 | 0.76975824 | 0.09490066 | poor | very poor |
| 90 | 0.24281905 | 0.76237608 | 0.07733859 | poor | very poor |
| 91 | 0.2162437 | 0.75863569 | 0.06163872 | poor | very poor |
| 92 | 0.1907576 | 0.75925007 | 0.04792685 | poor | very poor |
| 93 | 0.16655604 | 0.765073 | 0.03625917 | poor | very poor |
| 94 | 0.14381819 | 0.77716093 | 0.0266144 | poor | very poor |
| 95 | 0.1227007 | 0.79686126 | 0.01889346 | poor | very poor |
| 96 | 0.10333146 | 0.82593962 | 0.01292757 | poor | very poor |
| 97 | 0.08580407 | 0.86676609 | 0.00849403 | poor | very poor |
| 98 | 0.07017342 | 0.92259329 | 0.00533747 | poor | very poor |
| 99 | 0.05645281 | 0.99798043 | 0.00319337 | poor | very poor |
| 100 | 0.04461294 | 1 | 0.00181027 | poor | very poor | apCL - Four (4) Stratification System Patient Data Analysis

| apCL2_score | Survival probability | Upper 95% confidence interval | Lower 95% confidence interval | Prognosis group | Prognosis group 2 |
|---|---|---|---|---|---|
| 0 | 0.93 | 1.00 | 0.79 | good | good |
| 1 | 0.94 | 1.00 | 0.84 | good | good |
| 2 | 0.94 | 1.00 | 0.85 | good | good |
| 3 | 0.94 | 1.00 | 0.83 | good | good |
| 4 | 0.95 | 1.00 | 0.82 | good | good |
| 5 | 0.95 | 1.00 | 0.80 | good | good |
| 6 | 0.95 | 1.00 | 0.79 | good | good |
| 7 | 0.95 | 1.00 | 0.78 | good | good |
| 8 | 0.95 | 1.00 | 0.78 | good | good |
| 9 | 0.95 | 1.00 | 0.77 | good | good |
| 10 | 0.95 | 1.00 | 0.77 | good | good |
| 11 | 0.95 | 1.00 | 0.77 | good | good |
| 12 | 0.95 | 1.00 | 0.77 | good | good |
| 13 | 0.95 | 1.00 | 0.78 | good | good |
| 14 | 0.95 | 1.00 | 0.78 | good | good |
| 15 | 0.95 | 1.00 | 0.78 | good | good |
| 16 | 0.94 | 1.00 | 0.79 | good | good |
| 17 | 0.94 | 1.00 | 0.80 | good | good |
| 18 | 0.94 | 1.00 | 0.80 | good | good |
| 19 | 0.94 | 1.00 | 0.81 | good | good |
| 20 | 0.93 | 1.00 | 0.81 | good | good |
| 21 | 0.93 | 1.00 | 0.81 | good | good |
| 22 | 0.93 | 1.00 | 0.80 | good | good |
| 23 | 0.92 | 1.00 | 0.80 | good | good |
| 24 | 0.92 | 1.00 | 0.78 | good | good |
| 25 | 0.91 | 1.00 | 0.77 | moderate | moderate |
| 26 | 0.90 | 1.00 | 0.75 | moderate | moderate |
| 27 | 0.90 | 1.00 | 0.74 | moderate | moderate |
| 28 | 0.89 | 1.00 | 0.73 | moderate | moderate |
| 29 | 0.89 | 1.00 | 0.71 | moderate | moderate |
| 30 | 0.88 | 1.00 | 0.70 | moderate | moderate |
| 31 | 0.87 | 1.00 | 0.69 | moderate | moderate |
| 32 | 0.86 | 1.00 | 0.68 | moderate | moderate |
| 33 | 0.85 | 1.00 | 0.67 | moderate | moderate |
| 34 | 0.85 | 1.00 | 0.67 | moderate | moderate |
| 35 | 0.84 | 1.00 | 0.66 | moderate | moderate |
| 36 | 0.83 | 1.00 | 0.65 | moderate | moderate |
| 37 | 0.82 | 1.00 | 0.64 | moderate | moderate |
| 38 | 0.81 | 1.00 | 0.63 | moderate | moderate |
| 39 | 0.80 | 1.00 | 0.62 | moderate | moderate |
| 40 | 0.79 | 1.00 | 0.61 | moderate | moderate |
| 41 | 0.78 | 1.00 | 0.60 | moderate | moderate |
| 42 | 0.77 | 1.00 | 0.59 | moderate | moderate |
| 43 | 0.75 | 1.00 | 0.57 | moderate | moderate |
| 44 | 0.74 | 0.99 | 0.56 | moderate | moderate |
| 45 | 0.73 | 0.99 | 0.54 | moderate | moderate |
| 46 | 0.72 | 0.99 | 0.52 | moderate | moderate |
| 47 | 0.71 | 0.99 | 0.51 | moderate | moderate |
| 48 | 0.69 | 0.99 | 0.49 | moderate | moderate |
| 49 | 0.68 | 0.99 | 0.47 | moderate | moderate |
| 50 | 0.67 | 0.99 | 0.45 | poor | poor |
| 51 | 0.66 | 0.99 | 0.44 | poor | poor |
| 52 | 0.64 | 0.99 | 0.42 | poor | poor |
| 53 | 0.63 | 0.99 | 0.40 | poor | poor |
| 54 | 0.62 | 0.98 | 0.38 | poor | poor |
| 55 | 0.60 | 0.98 | 0.37 | poor | poor |
| 56 | 0.59 | 0.98 | 0.35 | poor | poor |
| 57 | 0.57 | 0.97 | 0.34 | poor | poor |
| 58 | 0.56 | 0.97 | 0.32 | poor | poor |
| 59 | 0.54 | 0.96 | 0.31 | poor | poor |
| 60 | 0.53 | 0.95 | 0.30 | poor | poor |
| 61 | 0.52 | 0.94 | 0.28 | poor | poor |
| 62 | 0.50 | 0.93 | 0.27 | poor | poor |
| 63 | 0.49 | 0.92 | 0.26 | poor | poor |
| 64 | 0.47 | 0.91 | 0.25 | poor | poor |
| 65 | 0.46 | 0.89 | 0.24 | poor | poor |
| 66 | 0.44 | 0.87 | 0.22 | poor | poor |
| 67 | 0.43 | 0.86 | 0.21 | poor | poor |
| 68 | 0.41 | 0.84 | 0.20 | poor | poor |
| 69 | 0.40 | 0.82 | 0.19 | poor | poor |
| 70 | 0.38 | 0.80 | 0.18 | poor | poor |
| 71 | 0.37 | 0.77 | 0.18 | poor | poor |
| 72 | 0.35 | 0.75 | 0.17 | poor | poor |
| 73 | 0.34 | 0.73 | 0.16 | poor | poor | apCL - Four (4) Stratification System Patient Data Analysis

| apCL2_score | Survival probability | Upper 95% confidence interval | Lowerr 95% confidence interval | Prognosis group | Prognosis group 2 |
|---|---|---|---|---|---|
| 74 | 0.32 | 0.71 | 0.15 | poor | poor |
| 75 | 0.31 | 0.69 | 0.14 | poor | very poor |
| 76 | 0.30 | 0.67 | 0.13 | poor | very poor |
| 77 | 0.28 | 0.65 | 0.12 | poor | very poor |
| 78 | 0.27 | 0.63 | 0.11 | poor | very poor |
| 79 | 0.25 | 0.61 | 0.11 | poor | very poor |
| 80 | 0.24 | 0.59 | 0.10 | poor | very poor |
| 81 | 0.23 | 0.58 | 0.09 | poor | very poor |
| 82 | 0.21 | 0.56 | 0.08 | poor | very poor |
| 83 | 0.20 | 0.55 | 0.07 | poor | very poor |
| 84 | 0.19 | 0.54 | 0.07 | poor | very poor |
| 85 | 0.18 | 0.53 | 0.06 | poor | very poor |
| 86 | 0.16 | 0.52 | 0.05 | poor | very poor |
| 87 | 0.15 | 0.52 | 0.04 | poor | very poor |
| 88 | 0.14 | 0.51 | 0.04 | poor | very poor |
| 89 | 0.13 | 0.51 | 0.03 | poor | very poor |
| 90 | 0.12 | 0.51 | 0.03 | poor | very poor |
| 91 | 0.11 | 0.51 | 0.02 | poor | very poor |
| 92 | 0.10 | 0.52 | 0.02 | poor | very poor |
| 93 | 0.09 | 0.52 | 0.02 | poor | very poor |
| 94 | 0.08 | 0.53 | 0.01 | poor | very poor |
| 95 | 0.08 | 0.55 | 0.01 | poor | very poor |
| 96 | 0.07 | 0.56 | 0.01 | poor | very poor |
| 97 | 0.06 | 0.58 | 0.01 | poor | very poor |
| 98 | 0.05 | 0.61 | 0.00 | poor | very poor |
| 99 | 0.05 | 0.64 | 0.00 | poor | very poor |
| 100 | 0.04 | 0.68 | 0.00 | poor | very poor |

BIBLIOGRAPHY

The following references are incorporated herein by reference in their entirety.

1. Quasar Collaborative Group, Gray R, Barnwell J, McConkey C, Hills R K, Williams N S, Kerr D J: Adjuvant chemotherapy versus observation in patients with colorectal cancer: a randomised study. Lancet 2007, 370: 2020-2029.
2. Benson A B, Schrag D, Somerfield M R, Cohen A M, Figueredo A T, Flynn P J, Krzyzanowska M K, Maroun J, McAllister P, Van Cutsem E, Brouwers M, Charette M, Haller D G: American Society of Clinical Oncology recommendations on adjuvant chemotherapy for stage II colon cancer. J Clin Oncol 2004, 22:3408-3419.
3. Wang Y, Jatkoe T, Zhang Y, Mutch M G, Talantov D, Jiang J, McLeod H L, Atkins D: Gene expression profiles and molecular markers to predict recurrence of Dukes' B colon cancer. J Clin Oncol 2004, 22:1564-1571.
4. Jiang Y, Casey G, Layery I C, Zhang Y, Talantov D, Martin-McGreevy M, Skacel M, Manilich E, Mazumder A, Atkins D, Delaney C P, Wang Y: Development of a clinically feasible molecular assay to predict recurrence of stage II colon cancer. The Journal of molecular diagnostics: JMD 2008, 10:346-354.
5. O'Connell M J, Layery I, Yothers G, Paik S, Clark-Langone K M, Lopatin M, Watson D, Baehner F L, Shak S, Baker J, Cowens J W, Wolmark N: Relationship between tumor gene expression and recurrence in four independent studies of patients with stage II/III colon cancer treated with surgery alone or surgery plus adjuvant fluorouracil plus leucovorin. J Clin Oncol 2010, 28:3937-3944.
6. Gray R G, Quirke P, Handley K, Lopatin M, Magill L, Baehner F L, Beaumont C, Clark-Langone K M, Yoshizawa C N, Lee M, Watson D, Shak S, Kerr D J: Validation Study of a Quantitative Multigene Reverse Transcriptase-Polymerase Chain Reaction Assay for Assessment of Recurrence Risk in Patients With Stage II Colon Cancer. J Clin Oncol 2011.
7. Bauer K M, Hummon A B, Buechler S: Right-side and left-side colon cancer follow different pathways to relapse. Mol. Carcinog. 2012, 51:411-421.
8. Meguid R A, Slidell M B, Wolfgang C L, Chang D C, Ahuja N: Is there a difference in survival between right- versus left-sided colon cancers? Ann Surg Oncol 2008, 15:2388-2394.
9. Buechler S A: Low expression of a few genes indicates good prognosis in estrogen receptor positive breast cancer. B M C Cancer 2009, 9:243.
10. Jorissen R N, Gibbs P, Christie M, Prakash S, Lipton L, Desai J, Kerr D, Aaltonen L A, Arango D, Kruhoffer M, Orntoft T F, Andersen C L, Gruidl M, Kamath V P, Eschrich S, Yeatman T J, Sieber O M: Metastasis-Associated Gene Expression Changes Predict Poor Outcomes in Patients with Dukes Stage B and C Colorectal Cancer. Clin Cancer Res 2009, 15:7642-7651.
11. Sorby L A, Andersen S N, Bukholm I R K, Jacobsen M B: Evaluation of suitable reference genes for normalization of real-time reverse transcription PCR analysis in colon cancer. J. Exp. Clin. Cancer Res. 2010, 29:144.
12. Chua S L, See Too W C, Khoo B Y, Few L L: UBC and YWHAZ as suitable reference genes for accurate normalisation of gene expression using MCF7, HCT116 and HepG2 cell lines. Cytotechnology 2011, 63:645-654.
13. Wickham H: *ggplot2: Elegant Graphics for Data Analysis (Use R!)*. 2nd edition. Springer; 2009.
14. Dexter D L, Spremulli E N, Fligiel Z, Barbosa J A, Vogel R, VanVoorhees A, Calabresi P: Heterogeneity of cancer cells from a single human colon carcinoma. Am. J. Med. 1981, 71:949-956.
15. Eshleman J R, Lang E Z, Bowerfind G K, Parsons R, Vogelstein B, Willson J K, Veigl M L, Sedwick W D, Markowitz S D: Increased mutation rate at the hprt locus accompanies microsatellite instability in colon cancer. Oncogene 1995, 10:33-37.

What is claimed is:

1. A colon cancer test for providing a treatment for a colon cancer patient having a right side colon cancer (RCC) or a left-side colon cancer (LCC), comprising:
   obtaining a RCC tissue specimen from a RCC patient or a LCC tissue specimen from a LCC patient, and performing the following steps:
   when the patient specimen is a RCC tissue specimen,
      measuring gene expression levels of RCC biomarker genes in the RCC tissue specimen with a panel of probes consisting of detectably labeled single-stranded polynucleotides complementary to mRNA or cDNA of a FAM69A, CDX2, FAM84A and ITGA3 gene to provide RCC test gene expression levels for each of the genes;
      normalizing each gene expression level against a control gene expression level to provide a normalized accelerated progression continuous risk (apCR) score for each of the genes;
      calculating an overall apCR patient score from the normalized apCR scores, and scaling the overall apCR patient score to provide a patient continuous risk score of from 0 to 100;
      treating the RCC patient with chemotherapy when the patient continuous risk score is 50 to 100, and not treating the RCC patient with chemotherapy when the patient continuous risk score is 0 to less than 25; and
   when the patient specimen is a LCC tissue specimen,
      measuring gene expression levels of LCC biomarker genes in the LCC tissue specimen with a panel of probes consisting of detectably labeled single-stranded polynucleotides complementary to mRNA or cDNA of a MMP3, WNT5A, NOX4, and IBSP gene to provide a patient specimen LCC test gene expression levels for each of the genes;
      normalizing each gene expression level against a control gene expression level to provide a normalized accelerated progression continuous risk (apCL) score for each of the genes;
      calculating an overall apCL patient score from the normalized gene-apCL scores, and scaling the overall apCL patient score to provide a patient continuous risk score of from 1 to 100; and
      treating the LCC patient with chemotherapy when the patient continuous risk score is 50 to 100, and not treating the patient with chemotherapy when the patient continuous risk score is 0 to less than 25.

2. The colon cancer test of claim 1 wherein the RCC colon cancer patient is a stage II RCC patient.

3. The colon cancer test of claim 1 wherein the RCC tissue specimen and LCC tissue specimen is a fresh-frozen tissue sample or a foimalin-fixed paraffin embedded (FFPE) tissue sample.

4. The colon cancer test of claim 1 wherein the chemotherapy comprises fluorouracil or folinic acid.

5. The method of claim 1 wherein the LCC patient is a stage II LCC patient.

6. The colon cancer test of claim 1 wherein the colon cancer patient is a stage III LCC patient.

7. The colon cancer test of claim 1 wherein the RCC patient is a stage III RCC patient.

* * * * *